(12) United States Patent
Nagamori et al.

(10) Patent No.: US 8,580,486 B2
(45) Date of Patent: Nov. 12, 2013

(54) SALT HAVING FLUORINE-CONTAINING CARBANION STRUCTURE, DERIVATIVE THEREOF, PHOTOACID GENERATOR, RESIST MATERIAL USING THE PHOTOACID GENERATOR, AND PATTERN FORMING METHOD

(75) Inventors: Masashi Nagamori, Fujimino (JP); Satoru Narizuka, Saitama (JP); Susumu Inoue, Ube (JP); Takashi Kume, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 182 days.

(21) Appl. No.: 12/922,300

(22) PCT Filed: Mar. 10, 2009

(86) PCT No.: PCT/JP2009/054479
§ 371 (c)(1),
(2), (4) Date: Dec. 3, 2010

(87) PCT Pub. No.: WO2009/113508
PCT Pub. Date: Sep. 17, 2009

(65) Prior Publication Data
US 2011/0070544 A1    Mar. 24, 2011

(30) Foreign Application Priority Data

Mar. 13, 2008  (JP) .................. 2008-064861

(51) Int. Cl.
| | | |
|---|---|---|
| *G03F 7/039* | (2006.01) | |
| *G03F 7/20* | (2006.01) | |
| *G03F 7/30* | (2006.01) | |
| *G03F 7/38* | (2006.01) | |
| *G03F 7/029* | (2006.01) | |

(52) U.S. Cl.
USPC ........... 430/921; 430/925; 430/942; 430/966; 430/270.1; 430/907; 430/910; 430/311; 430/326; 430/330; 568/32; 568/35; 560/103; 560/117; 560/222; 560/223

(58) Field of Classification Search
None
See application file for complete search history.

(56) References Cited

U.S. PATENT DOCUMENTS

| | | | |
|---|---|---|---|
| 3,704,311 A | 11/1972 | Koshar | |
| 5,554,664 A | 9/1996 | Lamanna et al. | |
| 5,696,224 A | 12/1997 | Benrabah et al. | |
| 6,777,160 B2 | 8/2004 | Sato et al. | |
| 7,674,567 B2 | 3/2010 | Yamamoto et al. | |
| 2007/0196766 A1 | 8/2007 | Wada | |

FOREIGN PATENT DOCUMENTS

| | | |
|---|---|---|
| JP | 8-81553 A | 3/1996 |
| JP | 11-501909 A | 2/1999 |
| JP | 2002-268223 A | 9/2002 |
| JP | 2004-85657 A | 3/2004 |
| JP | 2005-173464 A | 6/2005 |
| JP | 2007-86166 A | 4/2007 |
| JP | 2007-219411 A | 8/2007 |
| JP | 2007-241121 A | 9/2007 |
| JP | 2007-316600 A | 12/2007 |

OTHER PUBLICATIONS

International Search Report with partial translation dated Jun. 3, 2009 (nine (9) pages).
PCT/ISA/237 dated Jun. 3, 2009 (six (6) pages).
Korean Office Action with Japanese translation dated Apr. 23, 2012 (eleven (11) pages).
Chinese Office Action with Japanese translation dated Dec. 17, 2012 (sixteen (16) pages).

*Primary Examiner* — Sin J. Lee
(74) *Attorney, Agent, or Firm* — Crowell & Moring LLP

(57) ABSTRACT

There is provided an acid having a fluorine-containing carbanion structure or a salt having a fluorine-containing carbanion structure, which is represented by the following general formula (1).

[Chemical Formula 100]

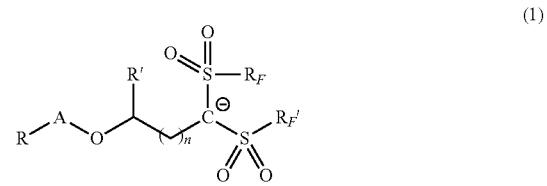

(1)

By using a photoacid generator for chemically amplified resist materials that generates this acid, it is possible to provide a photoacid generator which has a high sensitivity to the ArF excimer laser light or the like, of which acid (photo generated acid) to be generated has a sufficiently high acidity, and which has a high dissolution in resist solvent and a superior compatibility with resin, and a resist material containing such a photoacid generator.

22 Claims, No Drawings

SALT HAVING FLUORINE-CONTAINING CARBANION STRUCTURE, DERIVATIVE THEREOF, PHOTOACID GENERATOR, RESIST MATERIAL USING THE PHOTOACID GENERATOR, AND PATTERN FORMING METHOD

TECHNICAL FIELD

The present invention is a salt and its derivatives, having a novel fluorine-containing carbanion structure, which are preferably used as a photoacid generator of resist materials, etc., the photoacid generator, and a resist material using this, and a pattern forming method

BACKGROUND OF THE INVENTION

In recent years, the trend toward micro-scale pattern rule has been increasing with the trend toward large-scale integration and high-speed of LSI. The trend toward a shorter wavelength of the exposure light source lies behind it. For example, it has become possible to mass-produce DRAM (dynamic random-access memory) of 64M-bit (processing dimension is 0.25 µm or less) by the wavelength shortening from mercury lamp i-line (365 nm) to KrF excimer laser (248 nm). Furthermore, in order to realize the production of DRAM's having integration degrees of 256M and 1 G or greater, a lithography using ArF excimer laser (193 nm) has been studied on a full scale, and a 65 nm node device has been studied by a combination with a high NA lens (NA≥0.9). Although the use of $F_2$ laser having a wavelength of 157 nm had been named as a candidate for the production of the next 45 nm node devices, the application was postponed by many problems represented by cost increase of scanner, change of optical system, low etching resistance of resist, and the like. As an alternative to $F_2$ lithography, proposed was ArF immersion lithography. Now, its introduction is beginning. Furthermore, extreme ultraviolet (EUV) lithography is regarded as being promising in a design rule of 45 nm or less.

As a resist suitable for such exposure wavelength, "chemically amplified resist material" attracts much attention. This contains a radiosensitive acid generator (hereinafter referred to as "photoacid generator"), which generates an acid by radiation irradiation (hereinafter, referred to as "exposure"), and is a pattern-forming material that forms a pattern by making a difference in solubility between the exposed portion and the unexposed portion through a reaction using the acid generated by the exposure as a catalyst.

Various studies have also been conducted with respect to a photoacid generator used for such chemically amplified resist material. In case that a photoacid generator that generates an alkane or arenesulfonic acid, as used for chemically amplified resist materials, for which a conventional KrF excimer laser light is used as the light source, is used as a component of the above ArF chemically amplified resist materials, it is known that acid strength for severing an acid-labile group of the resin is not sufficient, resulting in no possibility of resolution at all, or it is known to be not suitable for device production due to low sensitivity.

Therefore, as a photoacid generator of ArF chemically amplified resist materials, one that generates a perfluoroalkanesulfonic acid, which is high in acid strength, is generally used. Perfluorooctanesulfonic acid, or its derivatives are, however, known as PFOS by its initials, and stability (undegradability) and hydrophobicity resulting from C—F bond, and ecological concentration and accumulation resulting from oleophilicity have become problems. Furthermore, a perfluoroalkanesulfonic acid having a carbon number of 5 or greater or its derivatives are also beginning to pose the above problems.

To deal with problems related to such PFOS, there is conducted by each company the development of a photoacid generator having a structure getting rid of PFOS skeleton, while maintaining level of acidity.

In Patent Publication 1, it is shown that a compound having an imide or methide acid is effective as an initiator, curing agent or catalyst, since it has a solubility in organic solvents and improves catalytic activity. After that, there have been disclosed many examples in which such compound having an imide or methide acid is used as a photoacid generator of chemically amplified resist materials (Patent Publication 2, Patent Publication 3, Patent Publication 4, Patent Publication 5, and Patent Publication 6). Furthermore, there is a report in Patent Publication 7 that a salt having a fluorine-containing carbanion that is analogous to methide anion (a carb anion having a carbon number of 1) acts as a photoacid generator. Furthermore, in Patent Publication 8, there is disclosed a method in which a polymerization is conducted by using a polymerizable cation, a photoacid generator itself is immobilized in a resist resin, and an imide or methide acid is used as the anion.

Patent Publication 1: Japanese Patent Application Publication 11-501909
Patent Publication 2: Japanese Patent Application Publication 2002-268223
Patent Publication 3: Japanese Patent Application Publication 2004-85657
Patent Publication 4: Japanese Patent Application Publication 2005-173464
Patent Publication 5: Japanese Patent Application Publication 2007-86166
Patent Publication 6: Japanese Patent Application Publication 2007-241121
Patent Publication 7: Japanese Patent Application Publication 2007-219411
Patent Publication 1: Japanese Patent Application Publication 2007-316600

SUMMARY OF THE INVENTION

In the case of conducting a precision line-width control, it has become important that chemically amplified resist is not only superior in resolution performance, but also superior in flatness of the film surface after the resist pattern formation. A chemically amplified resist that is inferior in flatness of the film surface lowers in pattern dimension system, as a result of transfer of roughness condition (nano edge roughness) of the film surface to substrate when resist pattern is transferred to substrate by a treatment such as etching. Therefore, it is known that at last electric characteristics of a device tend to be damaged.

Furthermore, in order to obtain a superior flatness too, a photoacid generator used for such chemically amplified resist materials is required to be homogeneously dispersed in a resist material. Therefore, solubility of photoacid generator in resist solvent and compatibility with resin are extremely important.

A photoacid generator using an imide or methide acid as anion, which has been developed up to now, is superior in solubility in resist solvent and compatibility with the resin. However, since an imide acid or methide acid (particularly bis(trifluoromethanesulfonium)imide acid or tris(trifluoromethanesulfonium)methide acid), which is generated after exposure, is volatile, there is a possibility that a high-price lens is attacked. Furthermore, in ArF immersion lithography, which is now becoming a mainstream, between lens and lens is saturated with water, but these imide acids or methide acids, which are superstrong acids, are water-soluble. Therefore, in this case too, there is a possibility that a high-price lens is attacked.

A photoacid generator disclosed in Publication 7 is capable of preventing these problems, but there are few descriptions as to the process for synthesizing an important carbanion moiety, and therefore the procurement easiness is unclear.

Thus, acids generated from conventional photoacid generators have not yet satisfied all of the above requirements.

The present inventors have eagerly repeated a study in order to solve the above task. As a result, we have found an acid having a fluorine-containing carbanion structure or a salt having a fluorine-containing carbanion structure, which is represented by the following general formula (1).

[Chemical Formula 1]

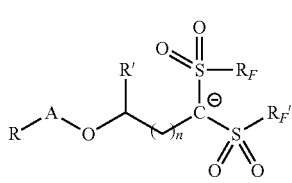

(1)

[In the general formula (1), n represents an integer of 1-3. R' represents a hydrogen atom or a $C_{1-3}$ substituted or unsubstituted alkyl group. R represents a $C_{1-10}$ straight-chain or branched alkyl group, a $C_{1-10}$ straight-chain or branched alkenyl group having a polymerizable double bond at an end portion at least, a $C_{3-20}$ alicyclic organic group, an organic group formed of a $C_{3-20}$ alicyclic organic group and a straight-chain alkylene group, a $C_{3-30}$ monocyclic or polycyclic lactone, or a $C_{6-20}$ aryl group (Herein, hydrogen atoms on the alkyl group, the alkenyl group, the alicyclic organic group, the organic group formed of the alicyclic organic group and the straight-chain alkylene group, the monocyclic or polycyclic lactone, and the aryl group may partially or entirely be replaced with fluorine, hydroxyl group, hydroxycarbonyl group, or $C_{1-6}$ straight-chain, branched or cyclic alkoxy group. Furthermore, two hydrogen atoms on the same carbon constituting the alkyl group, the alkenyl group, the alicyclic organic group, or the organic group formed of the alicyclic organic group and the straight-chain alkylene group may be replaced with a single oxygen atom to make a keto group. Furthermore, one of the hydrogen atoms on the alkyl group may be replaced with 2-acryloyloxy group or 2-methacryloyloxy group). A represents any one group of

[Chemical Formula 2]

Each of $R_F$ and $R_F{}'$ independently represents a $C_{1-4}$ perfluoroalkyl group.]

In particular, it has been found that the acid having a fluorine-containing carbanion structure represented by the following general formula (4) is an acid that is sufficiently high in strength and is useful for the resist pattern formation, although the fluorine content is relatively low (six).

[Chemical Formula 3]

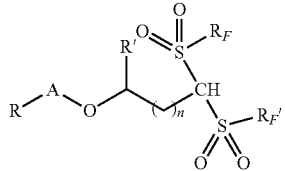

(4)

[In the above general formula (4), n, R', R, A, $R_F$, and $R_F{}'$ have the same meanings as those of n, R', R, A, $R_F$, and $R_F{}'$ in the general formula (1).]

Furthermore, it has been found that a salt formed of a fluorine-containing carbanion and an onium ion, which is represented by the following general formula (2),

[Chemical Formula 4]

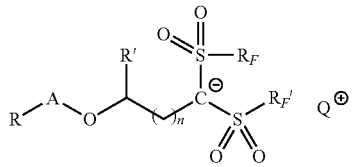

(2)

[In the above general formula (2), n, R', R, A, $R_F$, and $R_F{}'$ have the same meanings as those of n, R', R, A, $R_F$, and $R_F{}'$ in the general formula (1). $Q^+$ represents a sulfonium cation represented by the following general formula (a) or the following general formula (b), or an iodonium cation represented by the following general formula (c).

[Chemical Formula 5]

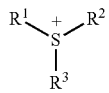

(a)

In the above general formula (a), $R^1$, $R^2$ and $R^3$ mutually independently represent substituted or unsubstituted $C_{1-10}$ straight-chain or branched alkyl groups, alkenyl groups or oxoalkyl groups; or substituted or unsubstituted $C_{6-18}$ aryl groups, aralkyl groups or aryloxoalkyl groups; or any two or more of $R^1$, $R^2$ and $R^3$ may be connected with each other to form a ring together with the sulfur atom in the formula.

[Chemical Formula 6]

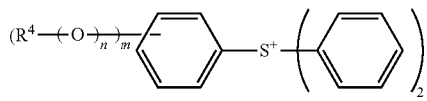

(b)

In the above general formula (b), $R^4$ represents a substituted or unsubstituted $C_{1-20}$ straight-chain, branched or cyclic alkyl group or alkenyl group; or substituted or unsubstituted $C_{6-14}$ aryl group. m represents an integer of 1-5, and n represents 0 (zero) or 1. As a substituent of $R^4$, it may contain a carbonyl group, hydroxyl group, ester, lactone, amino group, amide group, ether linkage oxygen atom or the like.

[Chemical Formula 7]

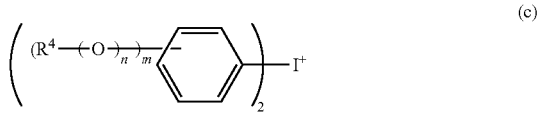

(c)

In the above general formula (c), $R^4$ represents a substituted or unsubstituted $C_{1-20}$ straight-chain, branched or cyclic alkyl group or alkenyl group; or substituted or unsubstituted $C_{6-14}$ aryl group. m represents an integer of 1-5, and n represents 0 (zero) or 1. As a substituent of $R^4$, it may contain a carbonyl group, hydroxyl group, ester, lactone, amino group, amide group, ether linkage oxygen atom or the like.] acts as a precursor compound (this is referred to as "photoacid generator") that generates an acid having the fluorine-containing carbanion structure by light and is capable of forming a resist pattern that has a even superior resolution as compared with conventional products. The resist pattern thus formed has also been found to achieve superior performances even in substrate adhesion and etching resistance.

An acid having a fluorine-containing carbanion structure or a salt having a fluorine-containing carbanion structure, which is represented by the general formula (1), has main characteristics that it has two perfluoroalkanesulfonyl groups on the same carbon, and furthermore it has an oxygen-containing hydrocarbon-series substituent and a hydrogen atom. That is, two perfluoroalkanesulfonyl groups are directly bonded to the same carbon. With this, it is considered that there is a significant increase in strength of the acid formed of the carbon and a hydrogen atom and that there are provided solubility in the resist solvent and compatibility with the resin. On the other hand, it is possible to adjust boiling point and solubility of an acid having the fluorine-containing carbanion structure by using ingenuity with the oxygen-containing hydrocarbon-series substituent.

Furthermore, the inventors have found that an acid having a fluorine-containing carbanion structure or a salt having a fluorine-containing carbanion structure, which is represented by the general formula (1), can efficiently be produced by making an acid halide, acid anhydride, phosgene, isocyanate, sulfonyl halide, sulfonyl anhydride or the like act on a fluorine-containing alcohol represented by the general formula (10).

[Chemical Formula 8]

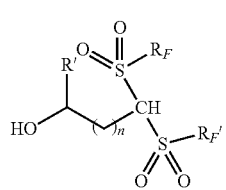

(10)

[In the above general formula (10), n, R', $R_F$ and $R_F'$ have the same meanings as those of n, R', $R_F$ and $R_F'$ in the general formula (1).]

Therefore, according to need, it is possible to introduce a substituent that is different in structure. With this, it is possible to freely control performances. Specifically, it is possible to suitably adjust boiling point of sulfonic acid to be generated, suppress its volatilization and dissolution in water, and control its diffusion distance by introducing a substituent having a large molecular weight or a bulky substituent. Furthermore, it is possible to freely improve dissolution in the resist solvent and compatibility with the base resin by introducing a substituent that is high in fat-solubility. Furthermore, by introducing a substituent having a double bond at an end, and in some cases by subjecting it to a copolymerization with another resist monomer, it is also possible to have an incorporation into the base resin and to suppress volatilization of an acid to be generated and dissolution in water, thereby contributing to solving the above task.

Furthermore, the present inventors have found a salt containing a fluorine-containing carbanion represented by the following general formula (3), which is useful as a common raw material, for producing the above-mentioned photoacid generator,

[Chemical Formula 9]

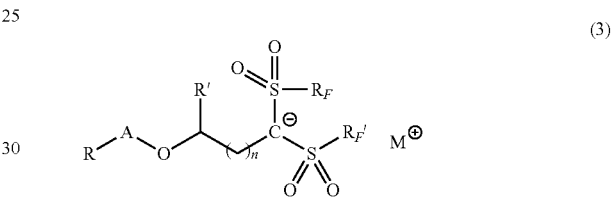

(3)

[In the above general formula (3), n, R', R, A, $R_F$, and $R_F'$ have the same meanings as those of n, R', R, A, $R_F$, and $R_F'$ in the general formula (1). $M^+$ represents a lithium ion, sodium ion, potassium ion, ammonium ion, or tetramethylammonium ion.].

Furthermore, the present inventors have found the invention of a resist material (composition) in which any of the above-mentioned photoacid generators has been combined with solvent and a specific base resin.

Furthermore, in connection with these findings, we have found each invention of a method for producing an acid having a fluorine-containing carbanion structure represented by the general formula (4) and a resist pattern forming method, thereby reaching accomplishment of the present invention.

That is, according to the present invention, there is provided an acid (first acid) having a fluorine-containing carbanion structure or a salt (first salt) having a fluorine-containing carbanion structure, which is represented by the following general formula (1).

[Chemical Formula 10]

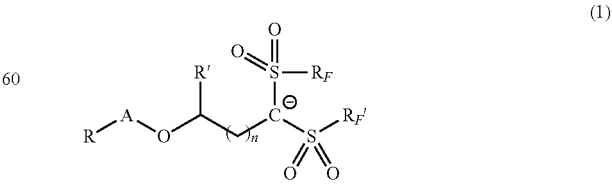

(1)

[In the above general formula (1), n represents an integer of 1-3. R' represents a hydrogen atom or a $C_{1-3}$ substituted or unsubstituted alkyl group. R represents a $C_{1-10}$ straight-chain or branched alkyl group, a $C_{1-10}$ straight-chain or branched alkenyl group having a polymerizable double bond at an end portion at least, a $C_{3-20}$ alicyclic organic group, an organic group formed of a $C_{3-20}$ alicyclic organic group and a straight-chain alkylene group, a $C_{3-30}$ monocyclic or polycyclic lactone, or a $C_{6-20}$ aryl group (Herein, hydrogen atoms on the alkyl group, the alkenyl group, the alicyclic organic group, the organic group formed of the alicyclic organic group and the straight-chain alkylene group, the monocyclic or polycyclic lactone, and the aryl group may partially or entirely be replaced with fluorine, hydroxyl group, hydroxycarbonyl group, or $C_{1-6}$ straight-chain, branched or cyclic alkoxy group. Furthermore, two hydrogen atoms on the same carbon constituting the alkyl group, the alkenyl group, the alicyclic organic group, or the organic group formed of the alicyclic organic group and the straight-chain alkylene group may be replaced with a single oxygen atom to make a keto group. Furthermore, one of the hydrogen atoms on the alkyl group may be replaced with 2-acryloyloxy group or 2-methacryloyloxy group). A represents any one group of

[Chemical Formula 11]

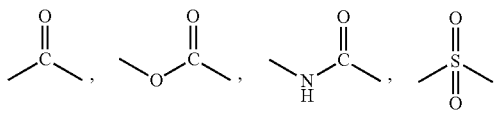

Each of $R_F$ and $R_F'$ independently represents a $C_{1-4}$ perfluoroalkyl group.]

Furthermore, according to the present invention, there is provided a salt (second salt) formed of a fluorine-containing carbanion and an onium ion, which is represented by the following general formula (2)

[Chemical Formula 12]

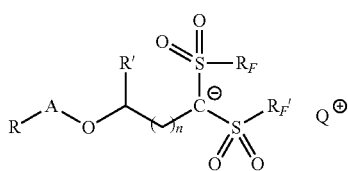

(2)

[In the above general formula (2), n, R', R, A, $R_F$, and $R_F'$ have the same meanings as those of n, R', R, A, $R_F$, and $R_F'$ in the general formula (1). $Q^+$ represents a sulfonium cation represented by the following general formula (a) or the following general formula (b), or an iodonium cation represented by the following general formula (c).

[Chemical Formula 13]

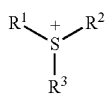

(a)

In the above general formula (a), $R^1$, $R^2$ and $R^3$ mutually independently represent substituted or unsubstituted $C_{1-10}$ straight-chain or branched alkyl groups, alkenyl groups or oxoalkyl groups; or substituted or unsubstituted $C_{6-18}$ aryl groups, aralkyl groups or aryloxoalkyl groups; or any two or more of $R^1$, $R^2$ and $R^3$ may be connected with each other to form a ring together with the sulfur atom in the formula.

[Chemical Formula 14]

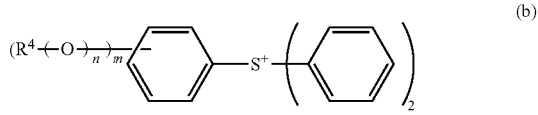

(b)

In the above general formula (b), $R^4$ represents a substituted or unsubstituted $C_{1-20}$ straight-chain, branched or cyclic alkyl group or alkenyl group; or substituted or unsubstituted $C_{6-14}$ aryl group. m represents an integer of 1-5, and n represents 0 (zero) or 1. As a substituent of $R^4$, it may contain a carbonyl group, hydroxyl group, ester, lactone, amino group, amide group, ether linkage oxygen atom or the like.

[Chemical Formula 15]

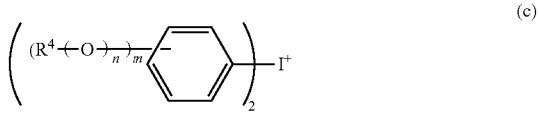

(c)

In the above general formula (c), $R^4$ represents a substituted or unsubstituted $C_{1-20}$ straight-chain, branched or cyclic alkyl group or alkenyl group; or substituted or unsubstituted $C_{6-14}$ aryl group. m represents an integer of 1-5, and n represents 0 (zero) or 1. As a substituent of $R^4$, it may contain a carbonyl group, hydroxyl group, ester, lactone, amino group, amide group, ether linkage oxygen atom or the like.]

Furthermore, according to the present invention, there is provided a salt (third salt) having a fluorine-containing carbanion represented by the following general formula (3).

[Chemical Formula 16]

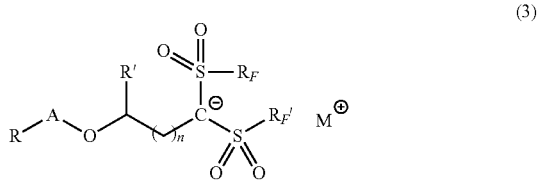

(3)

[In the above general formula (3), n, R', R, A, $R_F$, and $R_F'$ have the same meanings as those of n, R', R, A, $R_F$, and $R_F'$ in the general formula (1). $M^+$ represents a lithium ion, sodium ion, potassium ion, ammonium ion, or tetramethylammonium ion.]

Furthermore, according to the present invention, there is provided a photoacid generator (first photoacid generator) for chemically amplified resist materials, which is characterized by that an acid having a fluorine-containing carbanion structure represented by the following general formula (4) is generated by reacting to ultraviolet rays, far-ultraviolet rays, extreme ultraviolet rays (EUV), electron beam, X-ray, excimer laser, γ-ray, or a high energy ray of synchrotron radiation irradiation.

[Chemical Formula 17]

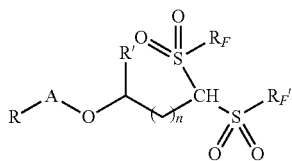

(4)

[In the above general formula (4), n, R', R, A, $R_F$, and $R_F'$ have the same meanings as those of n, R', R, A, $R_F$, and $R_F'$ in the general formula (1).]

Furthermore, according to the present invention, there is provided a photoacid generator (second photo generator) for chemically amplified resist materials, which is characterized by that it reacts to ultraviolet rays, far-ultraviolet rays, extreme ultraviolet rays (EUV), electron beam, X-ray, excimer laser, γ-ray, or a high energy ray of synchrotron radiation irradiation and that it contains the second salt.

Furthermore, according to the present invention, there is provided a method for producing an acid having the above fluorine-containing carbanion structure represented by the general formula (4) by irradiating the second photoacid generator with ultraviolet rays, far-ultraviolet rays, extreme ultraviolet rays (EUV), electron beam, X-ray, excimer laser, γ-ray, or a high energy ray of synchrotron radiation irradiation.

Furthermore, according to the present invention, in a resist material containing a base resin, a photoacid generator and a solvent, the resist material (first resist material), which is characterized by that this photoacid generator is the above first photoacid generator, is provided.

Furthermore, according to the present invention, in a resist material containing a base resin, a photoacid generator and a solvent, the resist material (second resist material), which is characterized by that this photoacid generator is the above second photoacid generator, is provided.

The first or second resist material may be a resist material (third resist material), which is characterized by that the base resin is a polymer prepared by polymerizing one monomer selected from the group consisting of olefins, fluorine-containing olefins, acrylates, methacrylates, fluorine-containing acrylates, fluorine-containing methacrylates, norbornene compounds, fluorine-containing norbornene compounds, styrene-series compounds, fluorine-containing styrene-series compounds, vinyl ethers and fluorine-containing vinyl ethers, or a copolymer prepared by copolymerizing at least two of the above monomers.

Furthermore, the first or second resist material may be a resist material (fourth resist material), which is characterized by that the base resin is a polymer compound containing a repeating unit represented by the following general formula (5).

[Chemical Formula 18]

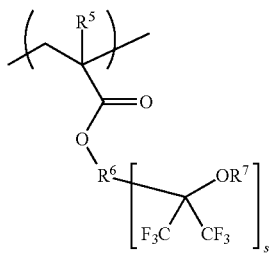

(5)

(In the above general formula (5), $R^5$ represents a hydrogen atom, halogen atom, hydrocarbon group, or fluorine-containing alkyl group. $R^6$ is an alkyl group that is straight-chain or optionally branched, an alkyl group having a ring structure, an aromatic ring, or a complex substituent of them, and a part of that may be fluorinated. $R^7$ is a hydrogen atom, and a hydrocarbon group optionally branched, a fluorine-containing alkyl group, or a ring form having an aromatic or aliphatic ring, and may contain bond such as oxygen or carbonyl. Furthermore, s represents an integer of 1-2.)

The fourth resist material may be a resist material (fifth resist material), which is characterized by that the repeating unit of the base resin is a repeating unit represented by the following general formula (6).

[Chemical Formula 19]

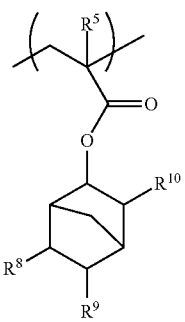

(6)

(In the above general formula (6), $R^5$ represents a hydrogen atom, halogen atom, hydrocarbon group, or fluorine-containing alkyl group. Any one of $R^8$, $R^9$ and $R^{10}$ is $CF_3C(CF_3)(OH)CH_2$— group, and the remaining two are hydrogen.)

Furthermore, the fourth resist material may be a resist material (sixth resist material), which is characterized by that the repeating unit of the base resin is a repeating unit represented by the following general formula (7).

[Chemical Formula 20]

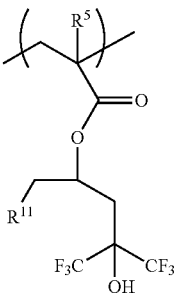

(7)

(In the above general formula (7), $R^5$ represents a hydrogen atom, halogen atom, hydrocarbon group, or fluorine-containing alkyl group. $R^{11}$ is a hydrogen atom, methyl group, ethyl group, n-propyl group, isopropyl group, n-butyl group, sec-butyl group, tert-butyl group, fluoromethyl group, difluoromethyl group, trifluoromethyl group, or perfluoroethyl group.)

Furthermore, the fourth resist material may be a resist material (seventh resist material), which is characterized by that the repeating unit of the base resin is a repeating unit represented by the following general formula (8).

[Chemical Formula 21]

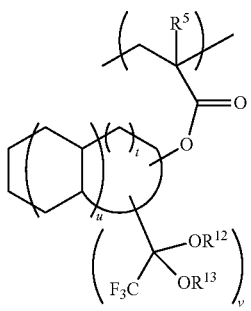

(8)

(In the above general formula (8), $R^5$ represents a hydrogen atom, halogen atom, hydrocarbon group, or fluorine-containing alkyl group. $R^{12}$ represents a methyl group or trifluoromethyl group. $R^{13}$ is a hydrogen atom, a $C_{1-25}$ straight-chain, branched or cyclic hydrocarbon group or a group containing an aromatic hydrocarbon group, and a part of that may contain fluorine atom, oxygen atom or carbonyl bond. u represents an arbitrary integer of 0-2. t and v represent arbitrary integers of 1-8, and satisfy v≤t+2. In case that $R^{12}$-$R^{13}$ are in plural number, $R^{12}$-$R^{13}$ may respectively the same or different.)

The first or second resist material may be a resist material (eighth resist material), which is characterized by that the base resin contains a repeating unit represented by the following general formula (9).

[Chemical Formula 22]

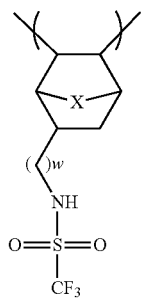

(9)

(In the above general formula (9), X represents any of —$CH_2$—, —O—, and —S—. w represents an integer of 2-6.)

Furthermore, the first or second resist material may be a resist material (ninth resist material), which is characterized by that the base resin contains a repeating unit represented by the following general formula (23).

[Chemical Formula 23]

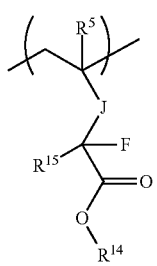

(23)

(In the above general formula (23), $R^5$ represents a hydrogen atom, halogen atom, hydrocarbon group, or fluorine-containing alkyl group. $R^{15}$ represents a fluorine atom or fluorine-containing alkyl group, and J represents a bivalent linking group. $R^{14}$ is a hydrogen atom, a $C_{1-25}$ straight-chain, branched or cyclic hydrocarbon group or a group containing an aromatic hydrocarbon group, and a part of that may contain fluorine atom, oxygen atom or carbonyl bond.)

Any one of the first to ninth resist materials may be a chemically amplified positive-type resist material (tenth resist), in which the base resin is insoluble or hardly soluble in a developing solution and becomes soluble in the developing solution by acid.

According to the present invention, there is provided a pattern forming method (first method), which is characterized by containing the step of applying any one of the first to tenth resist materials on a substrate, the step of exposing to a high energy ray having a wavelength of 300 nm or less through a photomask after a heating treatment, and the step of developing using a developing solution, after a heat treatment according to need.

The first method may be a pattern forming method (second method) characterized by that it is an immersion lithography in which an ArF excimer laser of a wavelength of 193 nm is used, and in which water or a liquid, apart from water, having a refractive index higher than refractive index in the air is inserted between a substrate coated with the resist material and a projector lens.

Furthermore, according to the present invention, there is provided 3-hydroxy-1,1-bis(trifluoromethanesulfonyl)butane represented by the following formula (11).

[Chemical Formula 24]

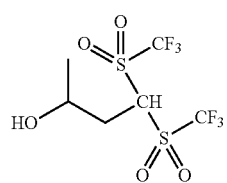

(11)

Furthermore, according to the present invention, there is provided 3-methacryloyloxy-1,1-bis(trifluoromethanesulfonyl)butane triphenylsulfonium salt represented by the following formula (12).

[Chemical Formula 25]

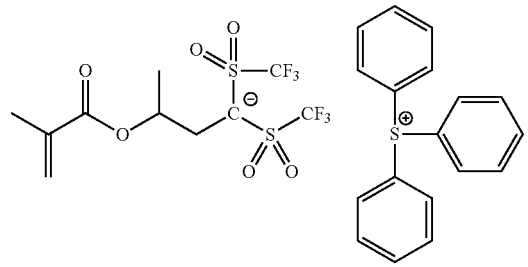

(12)

Furthermore, according to the present invention, there is provided 3-(1-adamantanecarbonyloxy)-1,1-bis(trifluoromethanesulfonyl)butane triphenylsulfonium salt represented by the following formula (13).

[Chemical Formula 26]

(13)

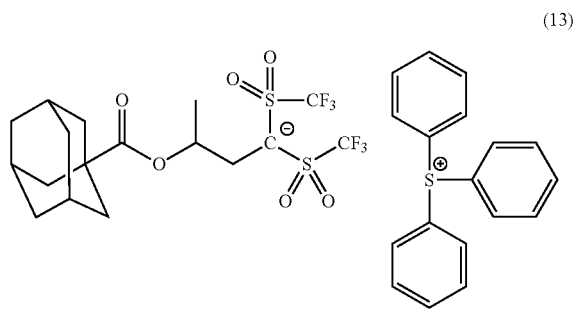

Furthermore, according to the present invention, there is provided 3-phenylcarbonyloxy-1,1-bis(trifluoromethane-sulfonyl)butane triphenylsulfonium salt represented by the following formula (22).

[Chemical Formula 27]

(22)

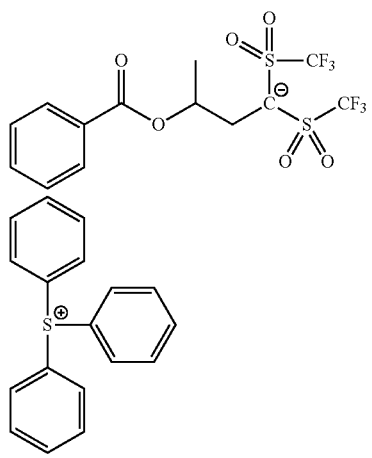

[Chemical Formula 28]

DETAILED DESCRIPTION

The salt formed of the fluorine-containing carbanion and the onium ion of the present invention has a small fear for ecological concentration and accumulation due to a low proportion of fluorine atoms in the structure, but it is sufficiently high in acidity of acid to be generated by exposure. Furthermore, it is possible to easily adjust the structure of this photo-generated acid. As a result, it is also possible to have a diffusion prevention or fixation of the photo-generated acid, and it is possible to avoid problems such as volatilization and dissolution into water of photo-generated acid.

Furthermore, in the case of forming a resist material by using as a photoacid generator this salt formed of the fluorine-containing carbanion and the onium ion, it has a high sensitivity to the ArF excimer laser light, and it shows superior performances in substrate adhesion and etching resistance. Then, it is possible to provide a photoacid generator (a salt formed of a fluorine-containing carbanion and an onium ion) that is superior in dissolution in resist solvent and compatibility with resin, and a resist material containing such photoacid generator. Furthermore, it is possible to provide a pattern forming method to obtain a good pattern shape by using such resist material.

The present invention shows the above-mentioned superior advantageous effects.

In the following, the best mode of embodiments of the present invention is explained. The present invention is, however, not limited to the following embodiments. It should be understood that those obtained by adding suitable changes, modifications and the like to the following embodiments, based on a normal knowledge of a person skilled in the art, are included in the scope of the present invention, to the extent of not diverging from the gist of the present invention.

Firstly, the relationship between the materials related to the present invention is shown in the following Fig. (1).

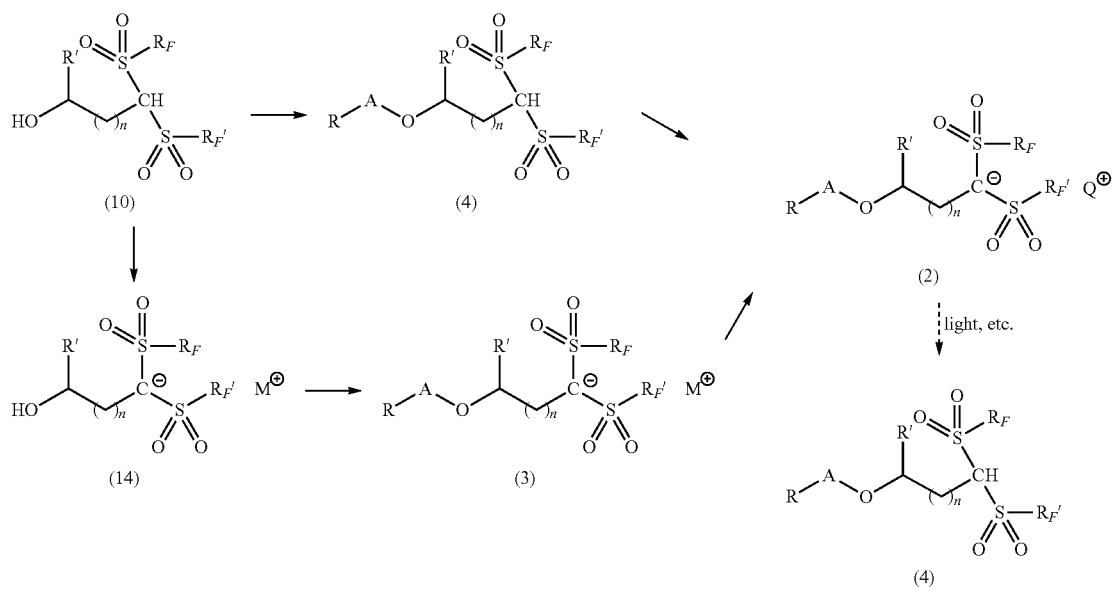

FIG. (1)

[In the above Fig. (1), n represents an integer of 1-3. R' represents a hydrogen atom or a $C_{1-3}$ substituted or unsubstituted alkyl group. R represents a $C_{1-10}$ straight-chain or branched alkyl group, a $C_{1-10}$ straight-chain or branched alkenyl group having a polymerizable double bond at an end portion at least, a $C_{3-20}$ alicyclic organic group, an organic group formed of a $C_{3-20}$ alicyclic organic group and a straight-chain alkylene group, a $C_{3-30}$ monocyclic or polycyclic lactone, or a $C_{6-20}$ aryl group (Herein, hydrogen atoms on the alkyl group, the alkenyl group, the alicyclic organic group, the organic group formed of the alicyclic organic group and the straight-chain alkylene group, the monocyclic or polycyclic lactone, and the aryl group may partially or entirely be replaced with fluorine, hydroxyl group, hydroxycarbonyl group, or $C_{1-6}$ straight-chain, branched or cyclic alkoxy group. Furthermore, two hydrogen atoms on the same carbon constituting the alkyl group, the alkenyl group, the alicyclic organic group, or the organic group formed of the alicyclic organic group and the straight-chain alkylene group may be replaced with a single oxygen atom to make a keto group. Furthermore, one of the hydrogen atoms on the alkyl group may be replaced with 2-acryloyloxy group or 2-methacryloyloxy group). A represents any one group of

[Chemical Formula 29]

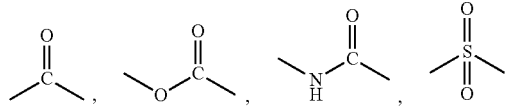

Each of $R_F$ and $R_F'$ independently represents a $C_{1-4}$ perfluoroalkyl group.

$Q^+$ represents a sulfonium cation represented by the following general formula (a) or the following general formula (b), or an iodonium cation represented by the following general formula (c).

[Chemical Formula 30]

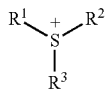

(a)

In the above general formula (a), $R^1$, $R^2$ and $R^3$ mutually independently represent substituted or unsubstituted $C_{1-10}$ straight-chain or branched alkyl groups, alkenyl groups or oxoalkyl groups; or substituted or unsubstituted $C_{6-18}$ aryl groups, aralkyl groups or aryloxoalkyl groups; or any two or more of $R^1$, $R^2$ and $R^3$ may be connected with each other to form a ring together with the sulfur atom in the formula.

[Chemical Formula 31]

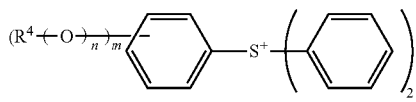

(b)

In the above general formula (b), $R^4$ represents a substituted or unsubstituted $C_{1-20}$ straight-chain, branched or cyclic alkyl group or alkenyl group; or substituted or unsubstituted $C_{6-14}$ aryl group. m represents an integer of 1-5, and n represents 0 (zero) or 1. As a substituent of $R^4$, it may contain a carbonyl group, hydroxyl group, ester, lactone, amino group, amide group, ether linkage oxygen atom or the like.

[Chemical Formula 32]

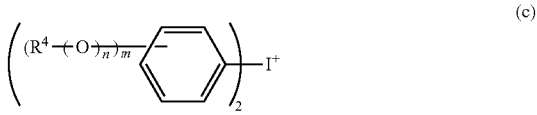

(c)

In the above general formula (c), $R^4$ represents a substituted or unsubstituted $C_{1-20}$ straight-chain, branched or cyclic alkyl group or alkenyl group; or substituted or unsubstituted $C_{6-14}$ aryl group. m represents an integer of 1-5, and n represents 0 (zero) or 1. As a substituent of $R^4$, it may contain a carbonyl group, hydroxyl group, ester, lactone, amino group, amide group, ether linkage oxygen atom or the like.

$M^+$ represents a lithium ion, sodium ion, potassium ion, ammonium ion, or tetramethylammonium ion. Each of $R_F$ and $R_F'$ independently represents a $C_{1-4}$ perfluoroalkyl group.]

As shown in the above Fig. 1, it is possible to generate the acid having a fluorine-containing carbanion structure, which is represented by the general formula (4), by irradiating a photoacid generator for chemically amplified resist materials, which is characterized by containing the salt formed of a fluorine-containing carbanion and an onium ion, which is represented by the general formula (2), with ultraviolet rays, far-ultraviolet rays, extreme ultraviolet rays (EUV), electron beam, X-ray, excimer laser, γ-ray, or a high energy ray of synchrotron radiation irradiation. On the other hand, it can also become a raw material for producing the salt formed of a fluorine-containing carbanion and an onium ion, which is represented by the general formula (2).

[Acid Having a Fluorine-Containing Carb Anion Structure]

The acid having a useful fluorine-containing carbanion structure, which is one of the raw material compounds of the photoacid generator in the present invention, and which can be generated by irradiating the photoacid generator in the present invention with ultraviolet rays, far-ultraviolet rays, extreme ultraviolet rays (EUV), electron beam, X-ray, excimer laser, γ-ray, or a high energy ray of synchrotron radiation irradiation, is one represented by the following general formula (4).

[Chemical Formula 33]

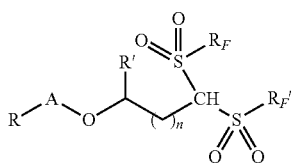

(4)

[In the above general formula (4), n, R', R, A, $R_F$ and $R_F'$ have the same meanings as those of n, R', R, A, $R_F$ and $R_F'$ in Fig. (1).]

Formed by release of proton from the acid having this fluorine-containing carbanion structure is a fluorine-containing carbanion structure represented by the general formula (1).

[Chemical Formula 34]

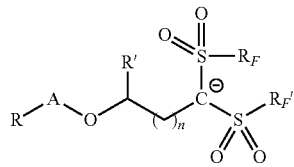

(1)

[In the above general formula (1), n, R', R, A, $R_F$ and $R_F'$ have the same meanings as those of n, R', R, A, $R_F$ and $R_F'$ in Fig. (1).]

Since the acid having a fluorine-containing carbanion structure of the present invention is a strong acid, it dissociates into a fluorine-containing carbanion represented by the formula (1) and a proton under an environment that a polar solvent or a resin is coexistent. In the present invention, however, it is also expressed as the general formula (4) for convenience.

Herein, R' represents a hydrogen atom or a $C_{1-3}$ substituted or unsubstituted alkyl group. Specifically, it is exemplified by hydrogen atom, methyl group, ethyl group, n-propyl group, isopropyl group, trifluoromethyl group, trifluoroethyl group, hexafluoroisopropyl group, etc. From the viewpoint of the production easiness, hydrogen atom, methyl group and ethyl group are preferable.

R represents a $C_{1-10}$ straight-chain or branched alkyl group, a $C_{1-10}$ straight-chain or branched alkenyl group having a polymerizable double bond at an end portion at least, a $C_{3-20}$ alicyclic organic group, an organic group formed of a $C_{3-20}$ alicyclic organic group and a straight-chain alkylene group, a $C_{3-30}$ monocyclic or polycyclic lactone, or a $C_{6-20}$ aryl group (Herein, hydrogen atoms on the alkyl group, the alkenyl group, the alicyclic organic group, the organic group formed of the alicyclic organic group and the straight-chain alkylene group, the monocyclic or polycyclic lactone, and the aryl group may partially or entirely be replaced with fluorine, hydroxyl group, hydroxycarbonyl group, or $C_{1-6}$ straight-chain, branched or cyclic alkoxy group. Furthermore, two hydrogen atoms on the same carbon constituting the alkyl group, the alkenyl group, the alicyclic organic group, or the organic group formed of the alicyclic organic group and the straight-chain alkylene group may be replaced with a single oxygen atom to make a keto group. Furthermore, one of the hydrogen atoms on the alkyl group may be replaced with 2-acryloyloxy group or 2-methacryloyloxy group).

Herein, as R is more specifically shown, as the $C_{1-10}$ straight-chain or branched alkyl group, it is possible to mention, for example, methyl group, ethyl group, n-propyl group, i-propyl group, n-butyl group, t-butyl group, n-pentyl group, n-hexyl group, n-heptyl group, n-octyl group, n-nonyl group, n-decyl group, etc.

As the $C_{1-10}$ straight-chain or branched alkenyl group having a double bond at an end portion at least, it is possible to mention, for example, vinyl group, 1-methylethenyl group, allyl group, 3-butenyl group, 1-methylallyl group, 2-methylallyl group, 4-pentenyl group, 5-hexenyl group, etc.

As the $C_{3-20}$ alicyclic organic group, it is possible to mention, for example, cyclopropyl group, cyclobutyl group, cyclopentyl group, cyclohexyl group, bornyl group, norbornyl group, adamantyl group, pinanyl group, thujyl group, caryl group, camphanyl group, etc.

The organic group formed of a $C_{3-20}$ alicyclic organic group and a straight-chain alkylene group represents an organic group in which an alicyclic organic group and a valence of a straight-chain alkylene group are combined. Specifically, it is possible to mention, for example, cyclopropylmethyl group, cyclobutylmethyl group, cyclopentylmethyl group, cyclohexylmethyl group, bornylmethyl group, norbornylmethyl group, adamantylmethyl group, etc.

As the $C_{3-30}$ monocyclic or polycyclic lactone, it is possible to mention γ-butyrolactone, γ-valerolactone, angelicalactone, γ-hexylactone, γ-heptalactone, γ-octalactone, γ-nonalactone, 3-methyl-4-octanolide (whiskey lactone), γ-decalactone, γ-undecalactone, γ-dodecalactone, γ-jasmolactone (7-decenolactone), δ-hexylactone, 4,6,6(4,4,6)-trimethyltetrahydropyran-2-one, δ-octalactone, δ-nonalactone, δ-decalactone, δ-2-decenolactone, δ-undecalactone, δ-dodecalactone, δ-tridecalactone, δ-tetradecalactone, lactoscatone, ε-decalactone, ε-dodecalactone, cyclohexyllactone, jasminelactone, cis-jasmonelactone, methyl γ-decalactone or the following.

[Chemical Formula 35]

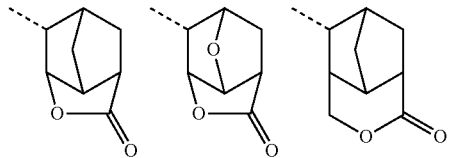

As the $C_{6-20}$ aryl group, it is possible to mention, for example, phenyl group, o-tolyl group, m-tolyl group, p-tolyl group, p-hydroxyphenyl group, 1-naphthyl group, 1-anthracenyl, benzyl group, etc.

Furthermore, each of $R_F$ and $R_F'$ independently represents a $C_{1-4}$ perfluoroalkyl group. Specifically, it represents a trifluoromethyl group, pentafluoroethyl group, heptafluoro-n-propyl group, heptafluoroisopropyl group, nonafluoro-n-butyl group, nonafluoro-sec-butyl group, or nonafluoro-tert-butyl group. In general, the more the number of carbons of the perfluoroalkyl group is, the more acidity can be expected. However, in view of the problem of ecological concentration and accumulation as is seen in the PFOS problem, it is preferable to have a fewer number of carbons of the perfluoroalkyl group. It is preferably trifluoromethyl group or pentafluoroethyl group. It is more preferably trifluoromethyl group.

Therefore, more specifically, a fluorine-containing carbanion structure represented by the general formula (1) can be exemplified as follows.

[Chemical Formula 36]

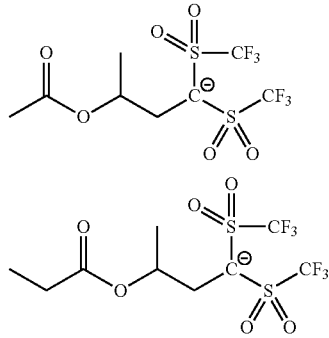

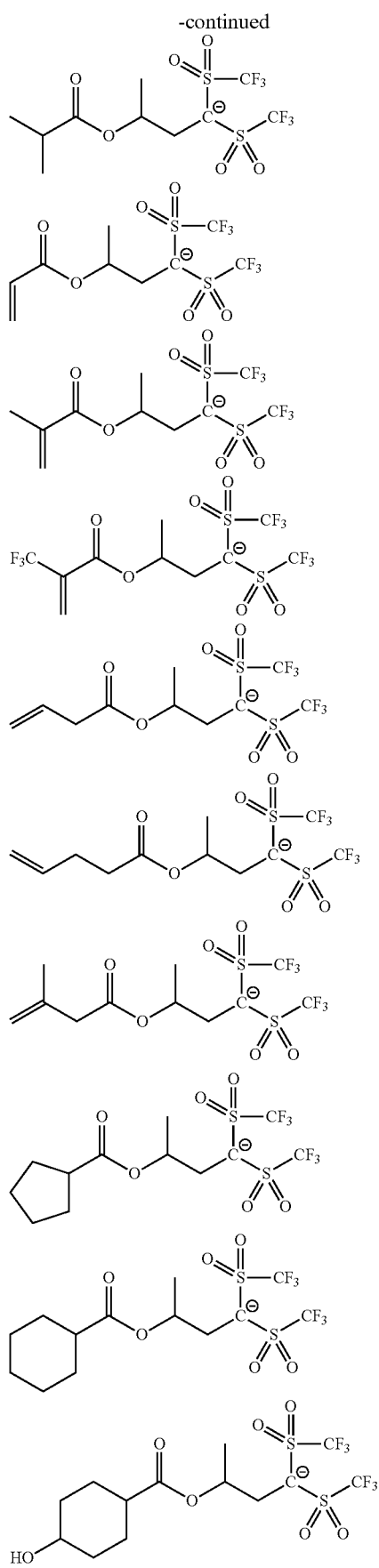
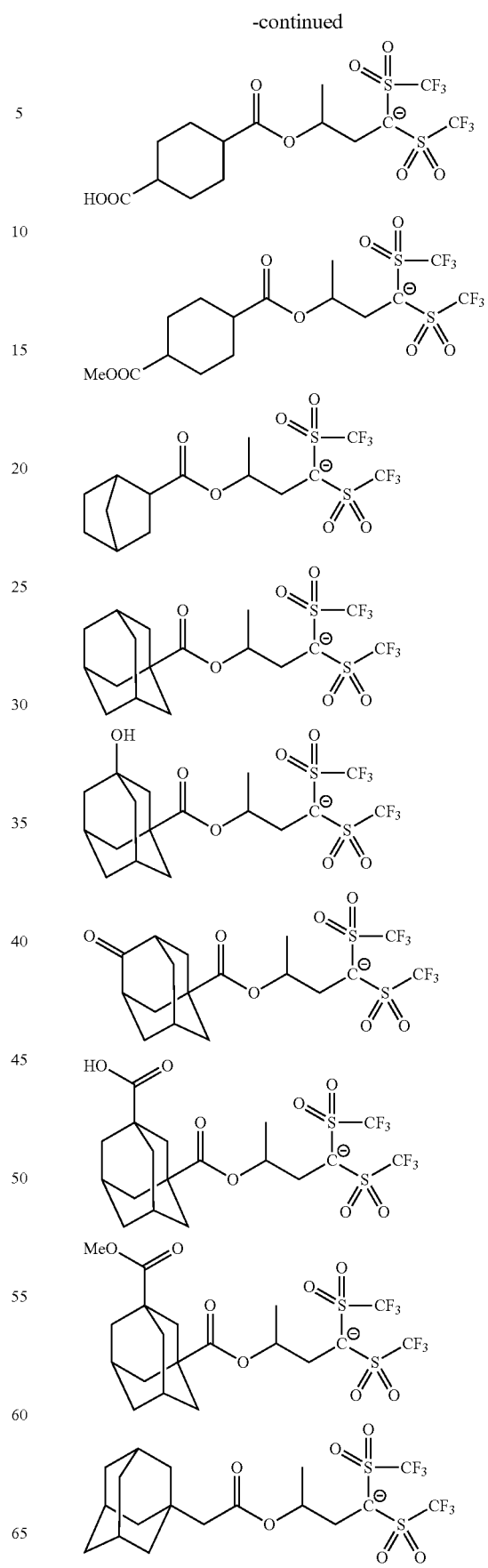

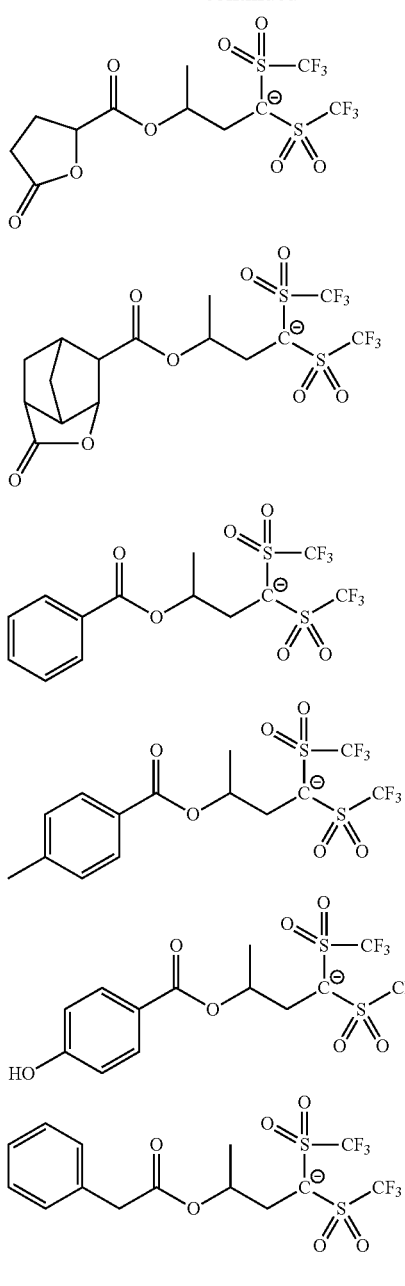
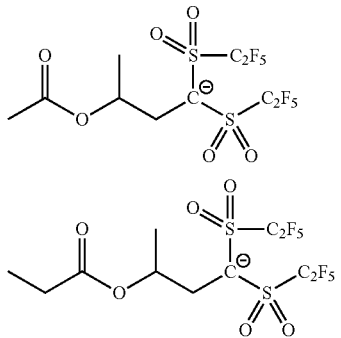
[Chemical Formula 37]
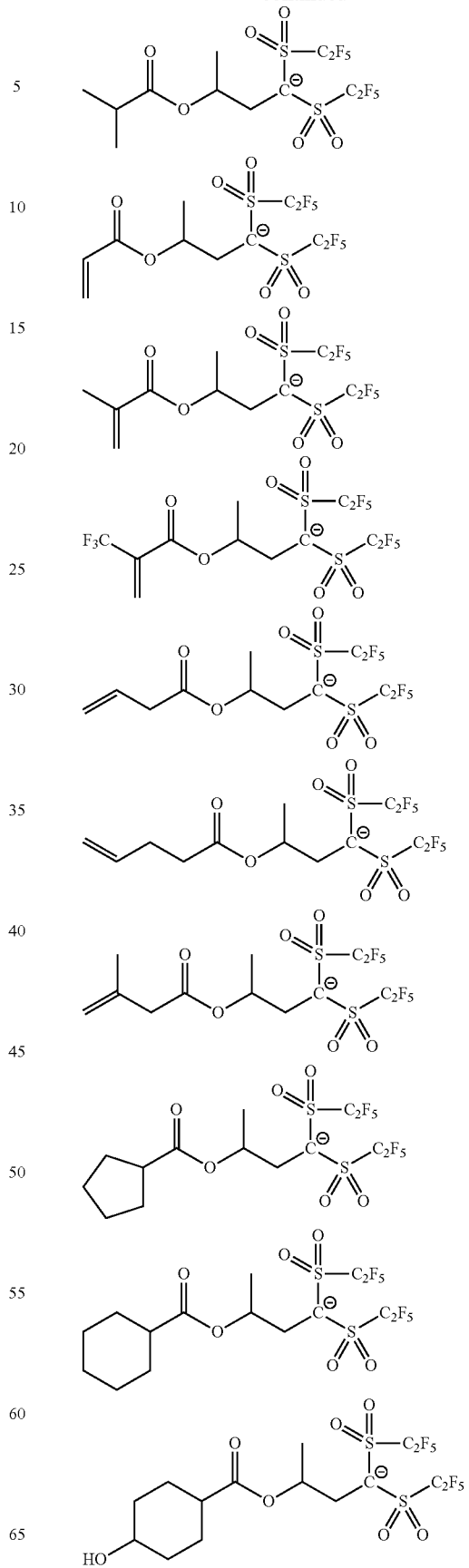

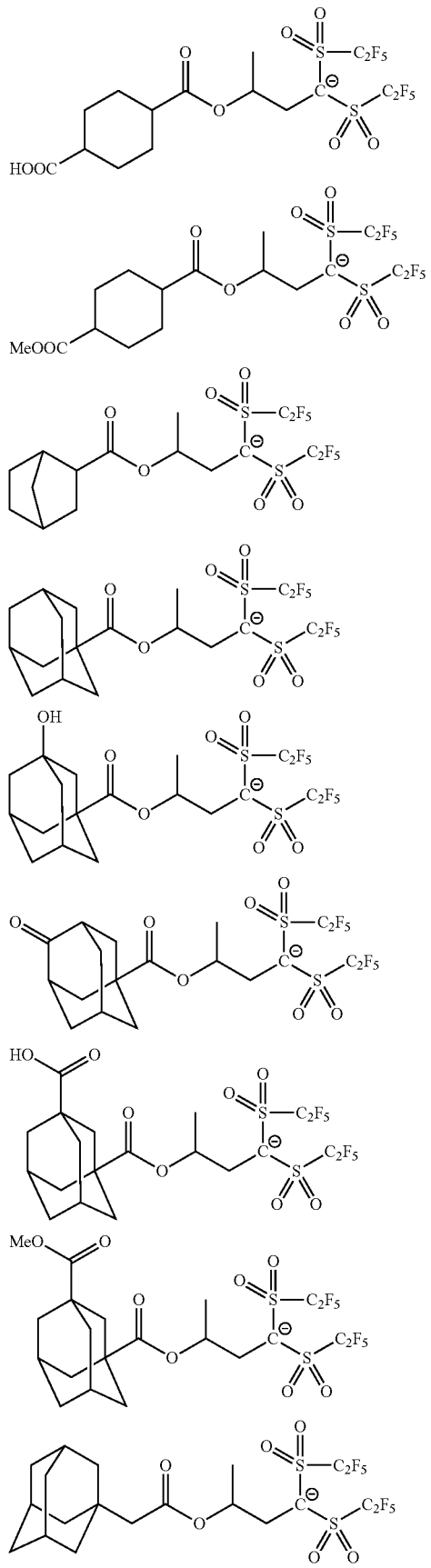
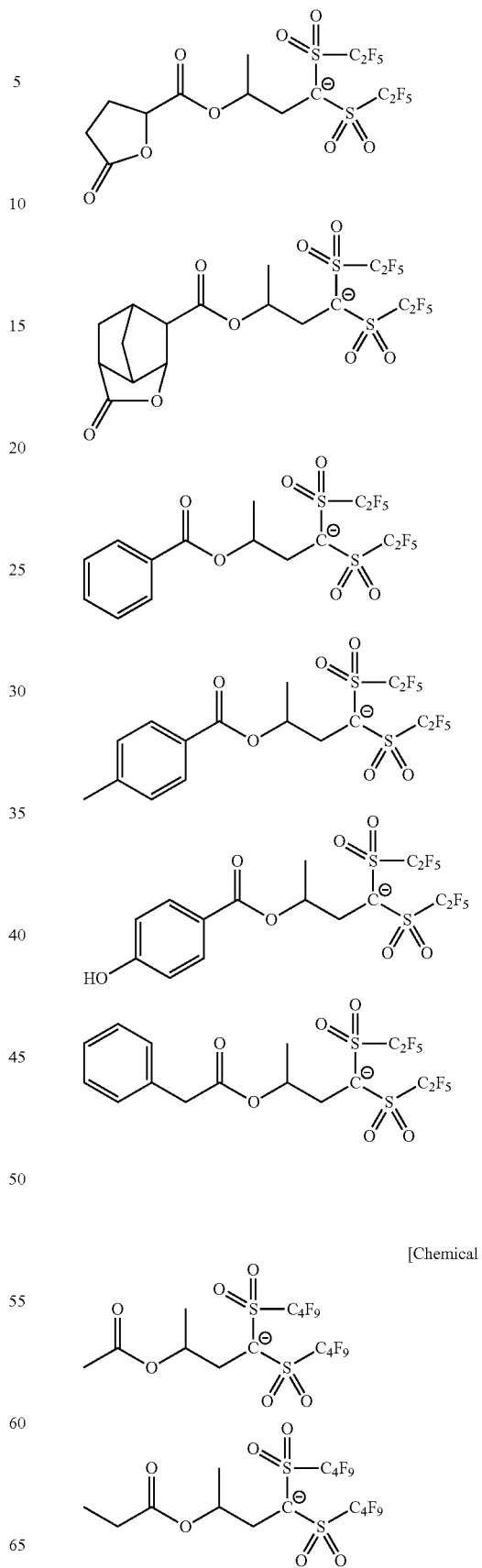
[Chemical Formula 38]
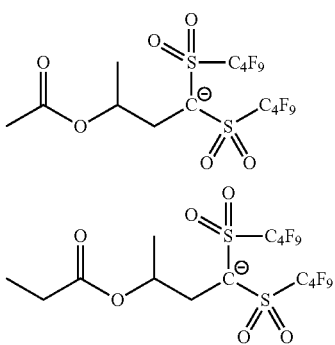

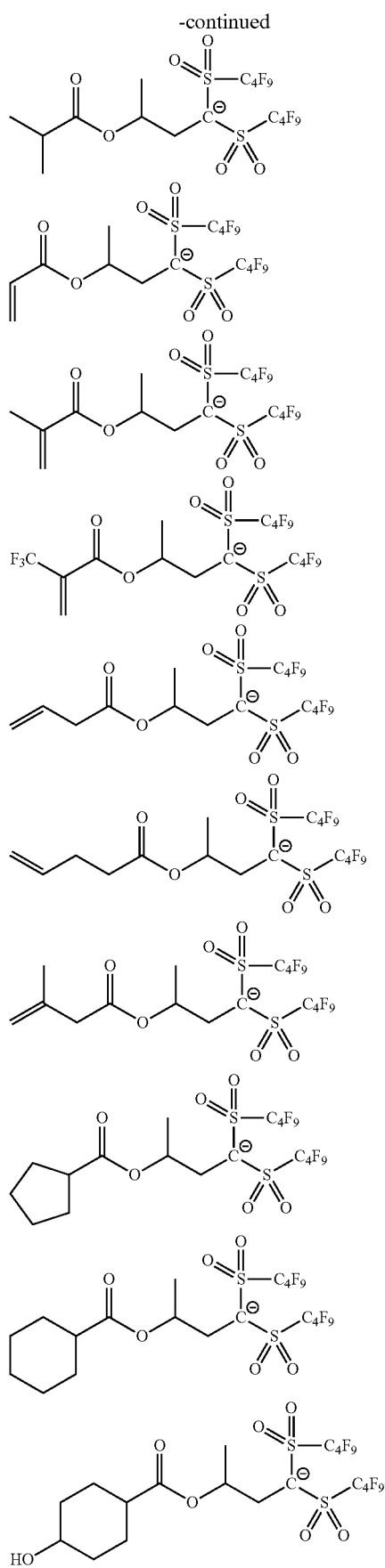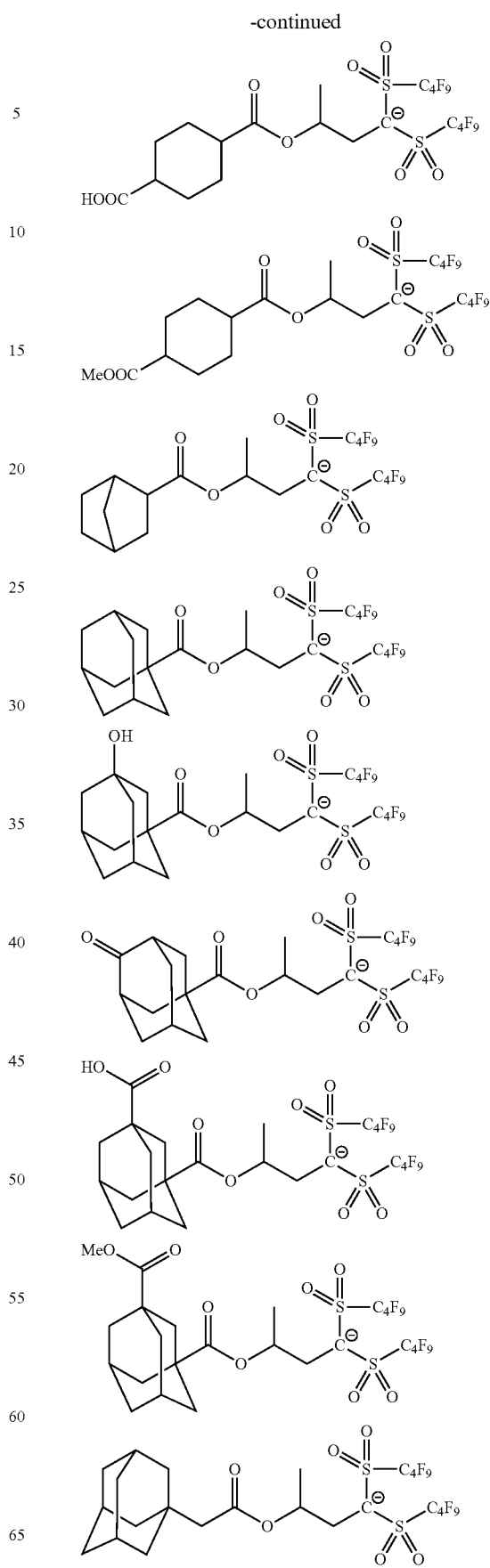

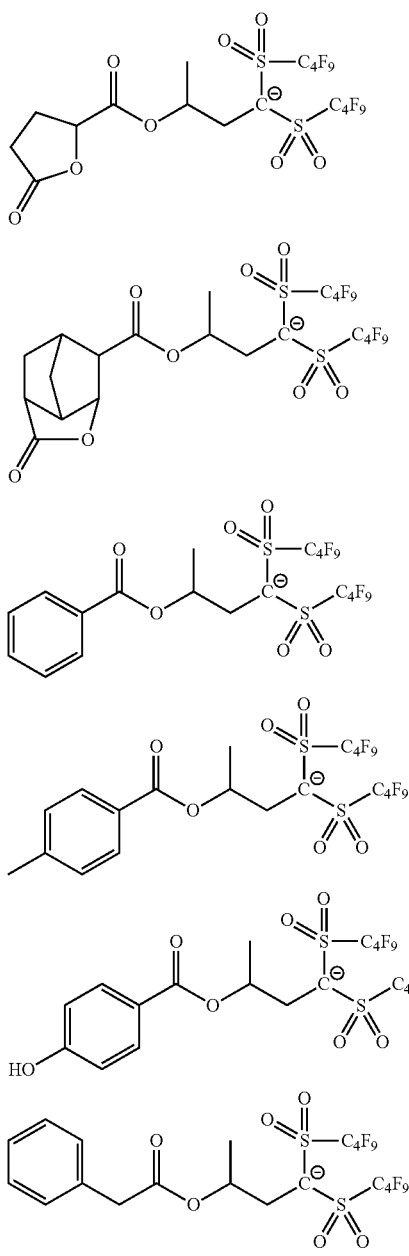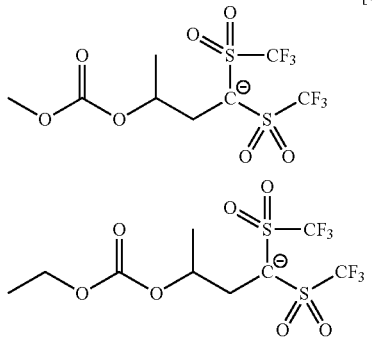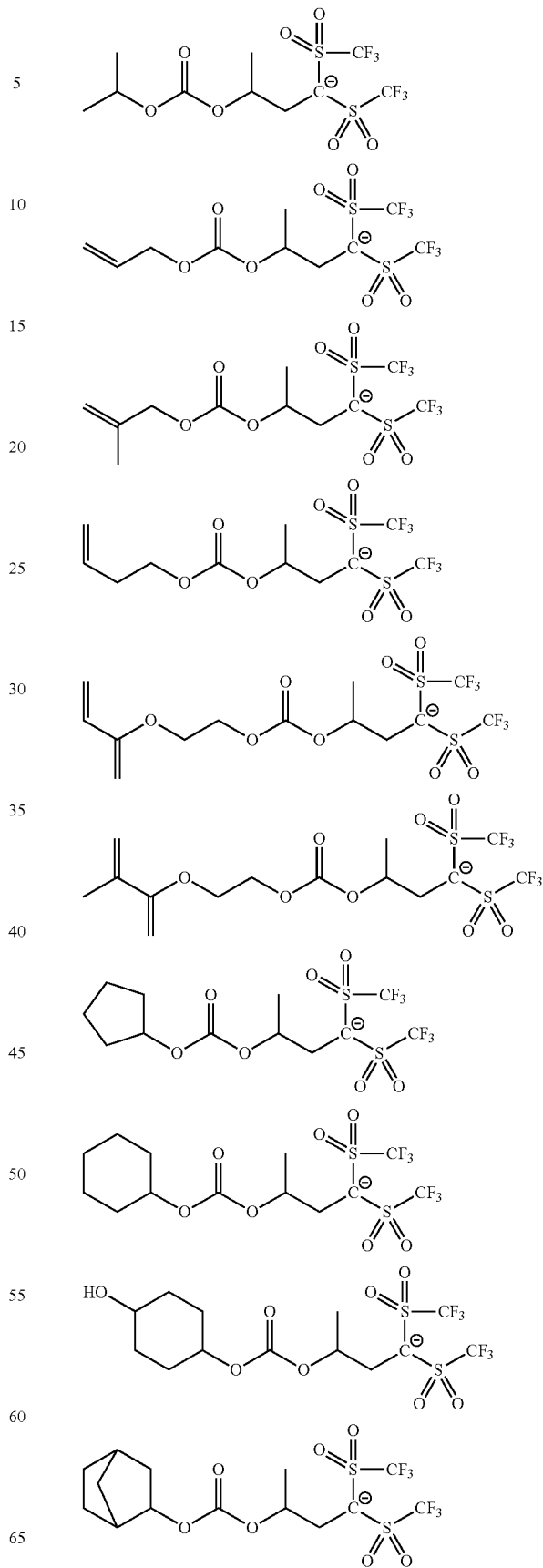

-continued
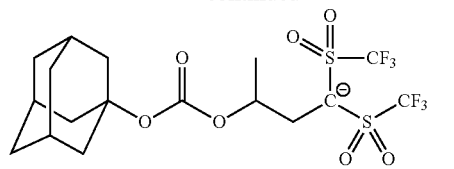
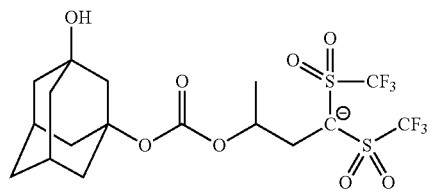
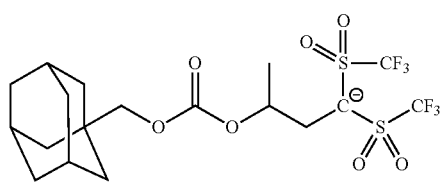
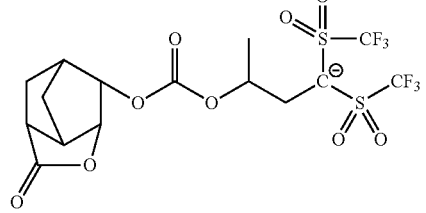
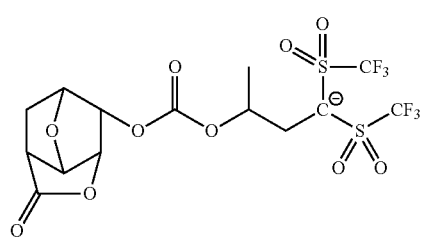
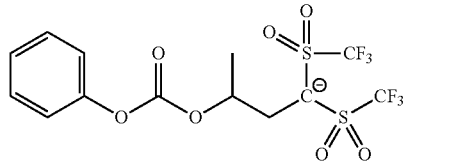
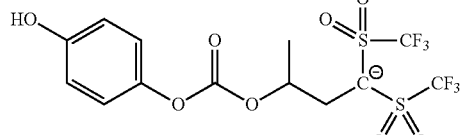
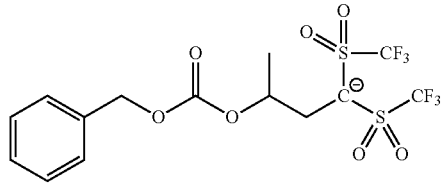
[Chemical Formula 40]
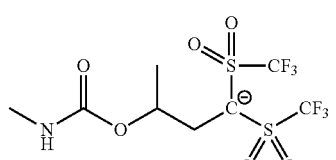
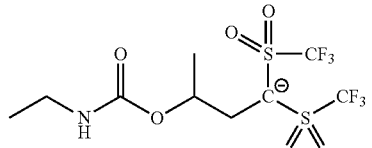
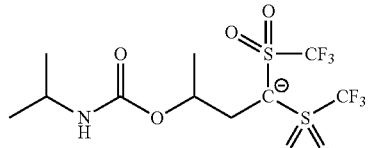
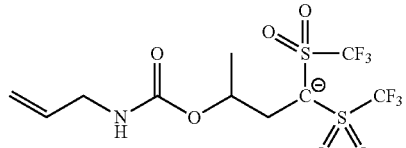
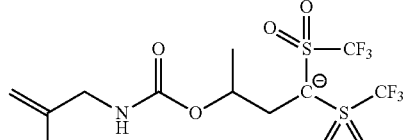
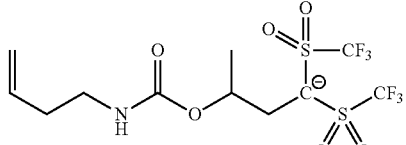
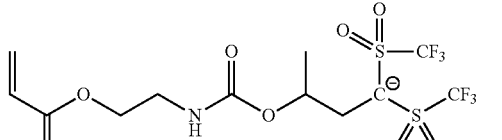
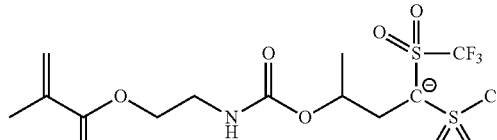
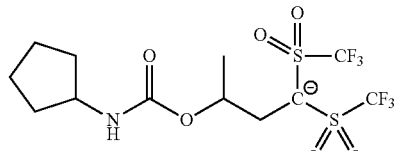
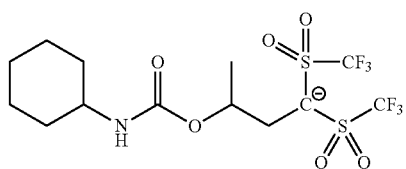

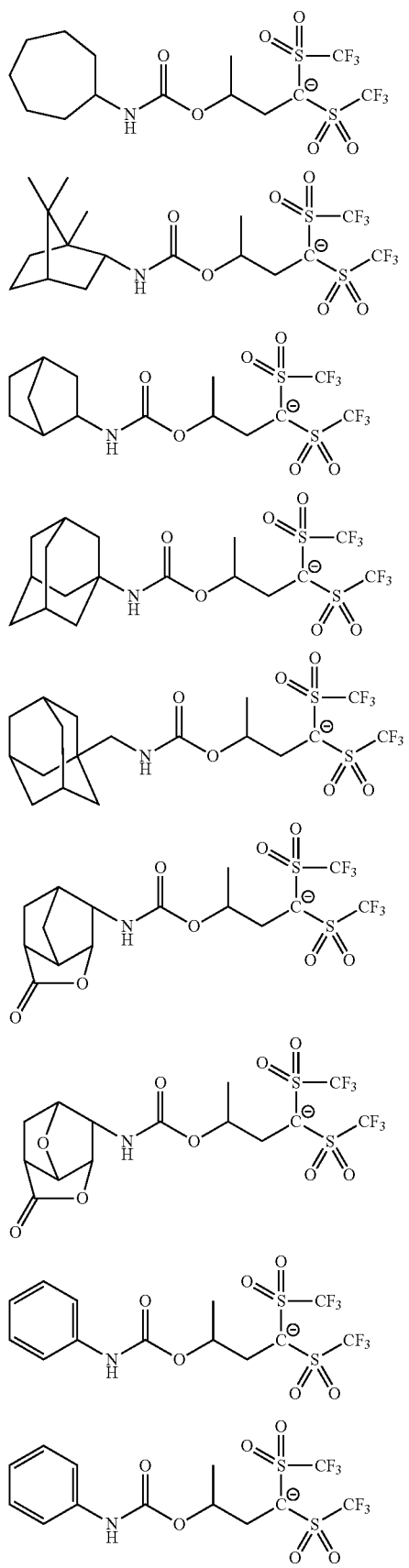
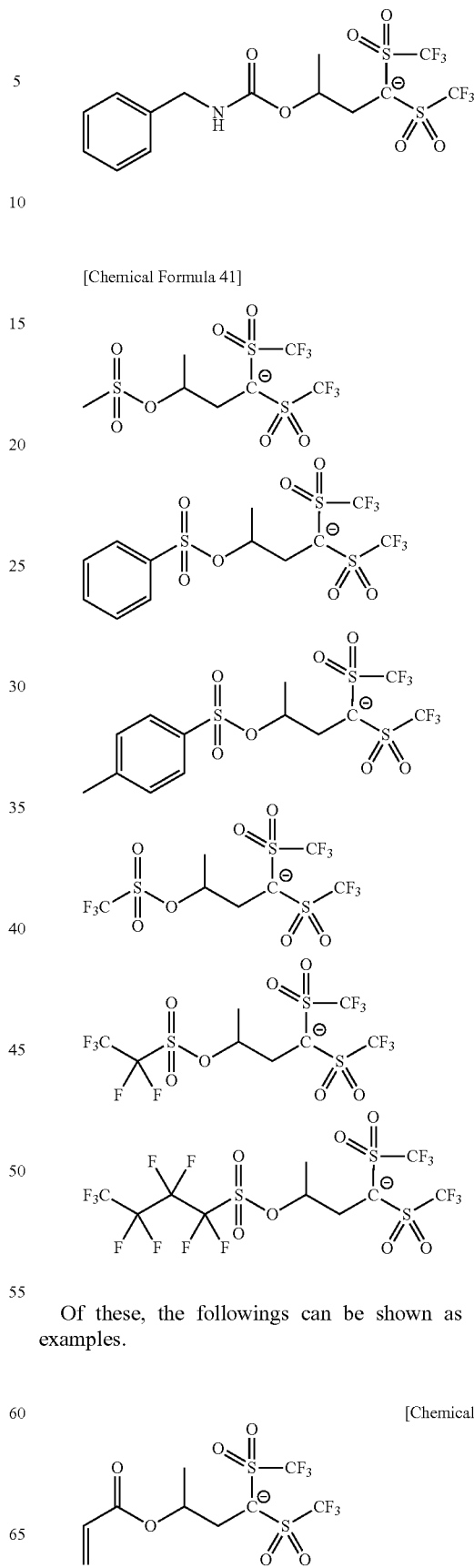
[Chemical Formula 41]
Of these, the followings can be shown as preferable examples.
[Chemical Formula 42]

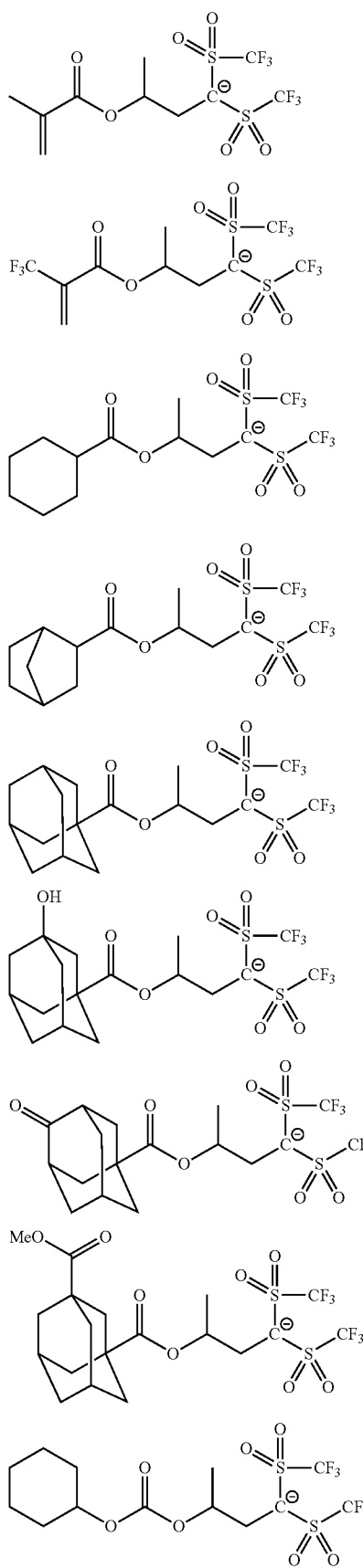
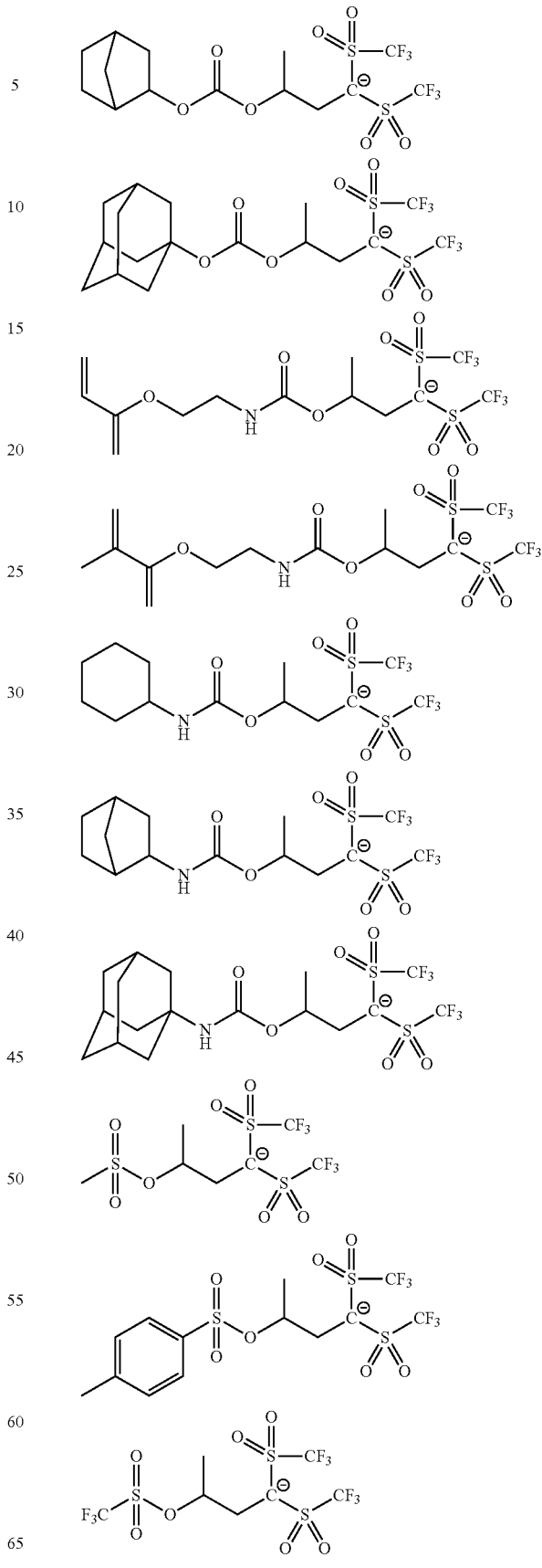

One obtained by protonating the fluorine-containing carbanion structure exemplified herein is an acid having the fluorine-containing carbanion structure represented by the general formula (4). As mentioned above, the acid having this fluorine-containing carbanion structure is one of raw material compounds of the photoacid generator and an acid (photogenerated acid) that can be generated by irradiating the photoacid generator in the present invention with ultraviolet rays, far-ultraviolet rays, extreme ultraviolet rays (EUV), electron beam, X-ray, excimer laser, γ-ray, or a high energy ray of synchrotron radiation irradiation.

[Salt Containing Fluorine-Containing Carbanion]

A salt containing the fluorine-containing carbanion, which is useful as one of raw material compounds of the photoacid generator in the present invention, is represented by the following general formula (3).

[Chemical Formula 43]

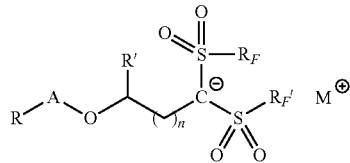

(3)

[In the above general formula (3), n, R', R, A, $R_F$, and $R_{F'}$ have the same meanings as those of n, R', R, A, $R_F$, and $R_{F'}$ in Fig. (1). $M^+$ represents a lithium ion, sodium ion, potassium ion, ammonium ion, or tetramethylammonium ion.]

Herein, the anion moiety in the general formula (3) is the above-mentioned fluorine-containing carbanion structure represented by the following general formula (1),

[Chemical Formula 44]

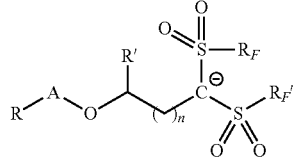

(1)

[In the above general formula (1), n, R', R, A, $R_F$, and $R_{F'}$ have the same meanings as those of n, R', R, A, $R_F$, and $R_{F'}$ in Fig. (1).]

and the specific structures shown as examples above can be shown again as examples.

As $M^+$ in the general formula (3), lithium ion, sodium ion, potassium ion, ammonium ion, or tetramethylammonium ion has been shown as examples. This is in consideration of synthesis easiness and easiness for isolating a salt containing the fluorine-containing carbanion. It is optional to use cations except this, for example, calcium ion, magnesium ion, etc. It is not particularly limited as long as it can exist as a stable salt.

In the case of using a salt containing the fluorine-containing carbanion as a raw material of the after-mentioned photoacid generator, it suffices that n, R', R, A, $R_F$, and $R_{F'}$ is made to agree with n, R', R, A, $R_F$, and $R_{F'}$ of the photoacid generator.

[Photoacid Generator]

The photoacid generator of the present invention reacts to ultraviolet rays, far-ultraviolet rays, extreme ultraviolet rays (EUV), electron beam, X-ray, excimer laser, γ-ray, or a high energy ray of synchrotron radiation irradiation, thereby generating an acid having a fluorine-containing carbanion structure represented by the following general formula (4), and is used as a photoacid generator for chemically amplified resist materials.

[Chemical Formula 45]

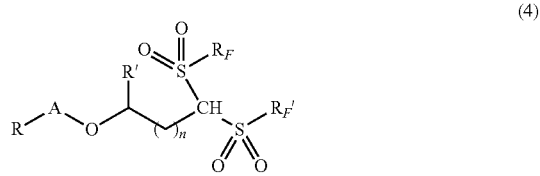

(4)

[In the above general formula (4), n, R', R, A, $R_F$, and $R_{F'}$ have the same meanings as those of n, R', R, A, $R_F$, and $R_{F'}$ in Fig. (1).]

Specific structures of the general formula (4) are as mentioned above.

[Salt Formed of Fluorine-Containing Carbanion and Onium Ion]

A salt formed of a fluorine-containing carbanion and an onium ion of the present invention is one of the photoacid generators of the present invention and is represented by the following general formula (2).

[Chemical Formula 46]

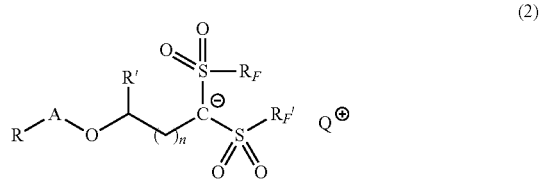

(2)

[In the above general formula (2), n, R', R, A, $R_F$, and $R_{F'}$ have the same meanings as those of n, R', R, A, $R_F$, and $R_{F'}$ in Fig. (1).]

$Q^+$ represents a sulfonium cation represented by the following general formula (a) or the following general formula (b), or an iodonium cation represented by the following general formula (c).

[Chemical Formula 47]

(a)

In the above general formula (a), $R^1$, $R^2$ and $R^3$ mutually independently represent substituted or unsubstituted $C_{1-10}$ straight-chain or branched alkyl groups, alkenyl groups or oxoalkyl groups; or substituted or unsubstituted $C_{6-18}$ aryl groups, aralkyl groups or aryloxoalkyl groups; or any two or more of $R^1$, $R^2$ and $R^3$ may be connected with each other to form a ring together with the sulfur atom in the formula.

[Chemical Formula 48]

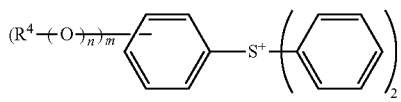

(b)

In the above general formula (b), $R^4$ represents a substituted or unsubstituted $C_{1-20}$ straight-chain, branched or cyclic alkyl group or alkenyl group; or substituted or unsubstituted $C_{6-14}$ aryl group. m represents an integer of 1-5, and n represents 0 (zero) or 1.

[Chemical Formula 49]

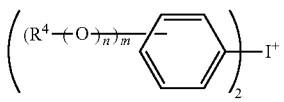

(c)

In the above general formula (c), $R^4$ represents a substituted or unsubstituted $C_{1-20}$ straight-chain, branched or cyclic alkyl group or alkenyl group; or substituted or unsubstituted $C_{6-14}$ aryl group. m represents an integer of 1-5, and n represents 0 (zero) or 1.)

In the following, the sulfonium cations represented by the general formula (a) and the general formula (b) and the iodonium cations represented by the general formula (c) and the general formula (d) are described in detail.

Sulfonium Cation Represented by the General Formula (a)

As $R^1$, $R^2$ and $R^3$ in the general formula (a), specifically the followings can be mentioned. As alkyl group, it is possible to mention methyl group, ethyl group, n-propyl group, isopropyl group, cyclopropyl group, n-butyl group, sec-butyl group, isobutyl group, tert-butyl group, n-pentyl group, cyclopentyl group, n-hexyl group, n-heptyl group, n-ethylhexyl group, cyclohexyl group, cycloheptyl group, 4-methylcyclohexyl group, cyclohexylmethyl group, n-octyl group, n-decyl group, 1-adamantyl group, 2-adamantyl group, bicyclo[2.2.1]hepten-2-yl group, 1-adamantanemethyl group, 2-adamantanemethyl group, etc. As alkenyl group, it is possible to mention vinyl group, allyl group, propenyl group, butenyl group, hexenyl group, cyclohexenyl group, etc. As oxoalkyl group, it is possible to mention 2-oxocyclopentyl group, 2-oxocyclohexyl group, 2-oxopropyl group, 2-oxoethyl group, 2-cyclopentyl-2-oxoethyl group, 2-cyclohexyl-2-oxoethyl group, 2-(4-methylcyclohexyl)-2-oxoethyl group, etc. As aryl group, it is possible to mention phenyl group, naphthyl group, thienyl group, etc.; alkoxy phenyl groups such as p-methoxyphenyl group, m-methoxyphenyl group, o-methoxyphenyl group, p-ethoxyphenyl group, p-tert-butoxyphenyl group, m-tert-butoxyphenyl group, etc.; alkylphenyl groups such as 2-methylphenyl group, 3-methylphenyl group, 4-methylphenyl group, ethylphenyl group, etc.; alkylnaphthyl groups such as methylnaphthyl group, ethylnaphthyl group, etc.; dialkylnaphthyl groups such as diethylnaphthyl group, etc.; dialkoxynaphthyl groups such as dimethoxynaphthyl group, diethoxynaphthyl group, etc. As aralkyl group, it is possible to mention benzyl group, 1-phenylethyl group, 2-phenylethyl group, etc. As aryloxoalkyl group, it is possible to mention 2-aryl-2-oxoethyl groups such as 2-phenyl-2-oxoethyl group, 2-(1-naphthyl)-2-oxoethyl group, 2-(2-naphthyl)-2-oxoethyl group, etc.

Furthermore, in case that any two or more of $R^1$, $R^2$ and $R^3$ are connected with each other to form a ring through the sulfur atom, it is possible to mention 1,4-butyrene, 3-oxa-1,5-pentyrene, etc. Furthermore, as the substituent, it is possible to mention an aryl group having a polymerizable substituent, such as acryloyloxy group, methacryloyloxy group, etc. Specifically, it is possible to mention 4-(acryloyloxy)phenyl group, 4-(methacryloyloxy)phenyl group, 4-vinyloxyphenyl group, 4-vinylphenyl group, etc.

As the sulfonium cation represented by the general formula (a) is shown more specifically, it is possible to mention triphenylsulfonium, (4-tert-butylphenyl)diphenylsulfonium, bis(4-tert-butylphenyl)phenylsulfonium, tris(4-tert-butylphenyl)sulfonium, (3-tert-butylphenyl)diphenylsulfonium, bis(3-tert-butylphenyl)phenylsulfonium, tris(3-tert-butylphenyl)sulfonium, (3,4-di-tert-butylphenyl)diphenylsulfonium, bis(3,4-di-tert-butylphenyl)phenylsulfonium, tris(3,4-di-tert-butylphenyl)sulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)diphenylsulfonium, (4-tert-butoxyphenyl)bis(4-dimethylaminophenyl)sulfonium, tris(4-dimethylaminophenyl)sulfonium, 2-naphthyldiphenylsulfonium, dimethyl(2-naphthyl)sulfonium, (4-hydroxyphenyl)dimethylsulfonium, (4-methoxyphenyl)dimethylsulfonium, trimethylsulfonium, (2-oxocyclohexyl)cyclohexylmethylsulfonium, trinaphthylsulfonium, tribenzylsulfonium, diphenylmethylsulfonium, dimethylphenylsulfonium, 2-oxo-2-phenylethylthiacyclopentanium, diphenyl-2-thienylsulfonium, 4-n-butoxynaphthyl-1-thiacyclopentanium, 2-n-butoxynaphthyl-1-thiacyclopentanium, 4-methoxynaphthyl-1-thiacyclopentanium, 2-methoxynaphthyl-1-thiacyclopentanium, etc. More preferably, it is possible to mention triphenylsulfonium, (4-tert-butylphenyl)diphenylsulfonium, (4-tert-butoxyphenyl)diphenylsulfonium, tris(4-tert-butylphenyl)sulfonium, (4-tert-butoxycarbonylmethyloxyphenyl)diphenylsulfonium, etc.

Furthermore, it is possible to mention 4-(methacryloyloxy)phenyldiphenylsulfonium, 4-(acryloyloxy)phenyldiphenylsulfonium, 4-(methacryloyloxy)phenyldimethylsulfonium, 4-(acryloyloxy)phenyldimethylsulfonium, etc. As to these polymerizable sulfonium cations, it is possible to refer to Japanese Patent Application Publication 4-230645 and Japanese Patent Application Publication 2005-84365, etc.

Sulfonium Cation Represented by the General Formula (b)

The position of the substituent of $R^4$—(O)n- group in the general formula (b) is not particularly limited, but 4-position or 3-position of the phenyl group is preferable. More preferably, it is 4-position. Herein, n is 0 (zero) or 1. As $R^4$, specifically it is possible to mention methyl group, ethyl group, n-propyl group, sec-propyl group, cyclopropyl group, n-butyl group, sec-butyl group, iso-butyl group, tert-butyl group, n-pentyl group, cyclopentyl group, n-hexyl group, cyclohexyl group, n-octyl group, n-decyl group, n-dodecyl group, 1-adamantyl group, 2-adamantyl group, bicyclo[2.2.1]hepten-2-yl group, phenyl group, 4-methoxyphenyl group, 4-tert-butylphenyl group, 4-biphenyl group, 1-naphthyl group, 2-naphthyl group, 10-antranyl group, 2-furanyl group, and in the case of n=1 acryloyl group, methacryloyl group, vinyl group, and allyl group.

As specific sulfonium cations, it is possible to mention (4-methylphenyl)diphenylsulfonium, (4-ethylphenyl)diphenylsulfonium, (4-cyclohexylphenyl)diphenylsulfonium, (4-n-hexylphenyl)diphenylsulfonium, (4-n-octyl)phenyldiphenylsulfonium, (4-methoxyphenyl)diphenylsulfonium, (4-ethoxyphenyl)diphenylsulfonium, (4-tert-butoxyphenyl)diphenylsulfonium, (4-cyclohexyloxyphenyl) diphenylsulfonium, (4-trifluoromethylphenyl) diphenylsulfonium, (4-trifluoromethyloxyphenyl)diphenylsulfonium, (4-tert-butoxycarbonylmethyloxyphenyl)diphenylsulfonium, etc.

Iodonium Cation Represented by the General Formula (c)

The position of the substituent of $R^4$—(O)n- group in the general formula (b) is not particularly limited, but 4-position or 3-position of the phenyl group is preferable. More preferably, it is 4-position. Herein, n is 0 (zero) or 1. As specific examples of $R^4$, it is possible to mention again the same ones as those of $R^4$ in the general formula (b).

As specific iodonium cations, it is possible to mention bis(4-methylphenyl)iodonium, bis(4-ethylphenyl)iodonium, bis(4-tert-butylphenyl)iodonium, bis(4-(1,1-dimethylpropyl)phenyl)iodonium, (4-methoxyphenyl)phenyliodonium, (4-tert-butoxyphenyl)phenyliodonium, 4-(acryloyloxy)phenylphenyliodonium, 4-(methacryloyloxy)phenylphenyliodonium, etc. In particular, bis(4-tert-butylphenyl)iodonium is preferably used.

Herein, the anion moiety in the general formula (2) is a fluorine-containing carbanion structure represented by the following general formula (1),

[Chemical Formula 50]

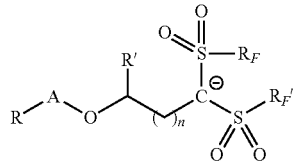

(1)

[In the above general formula (1), n, R', R, A, $R_F$, and $R_F'$ have the same meanings as those of n, R', R, A, $R_F$, and $R_F'$ in Fig. (1).]

and specific structures shown as examples above can be shown again as examples.

Combinations of preferable ones as the fluorine-containing carbanion structure represented by the general formula (1) with preferable ones as the onium ion $Q^+$ in the general formula (2) are preferable ones as a salt formed of the fluorine-containing carbanion and the onium ion, which is represented by the general formula (2). It can be exemplified as follows.

[Chemical Formula 51]

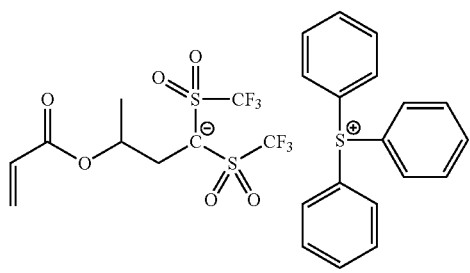

-continued

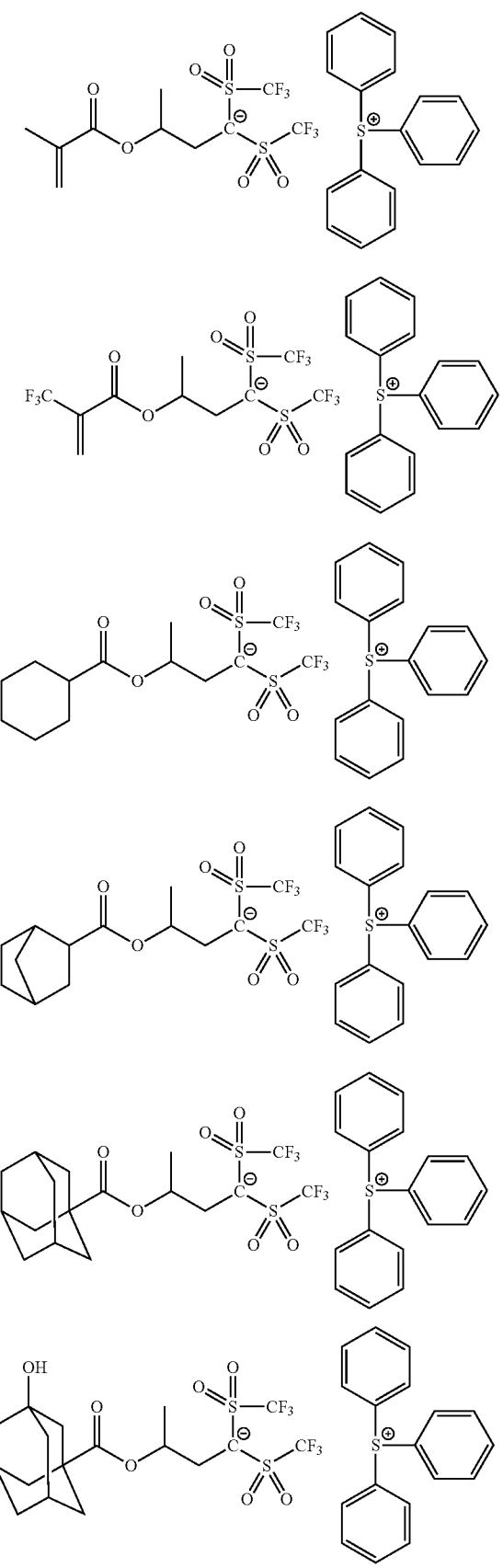

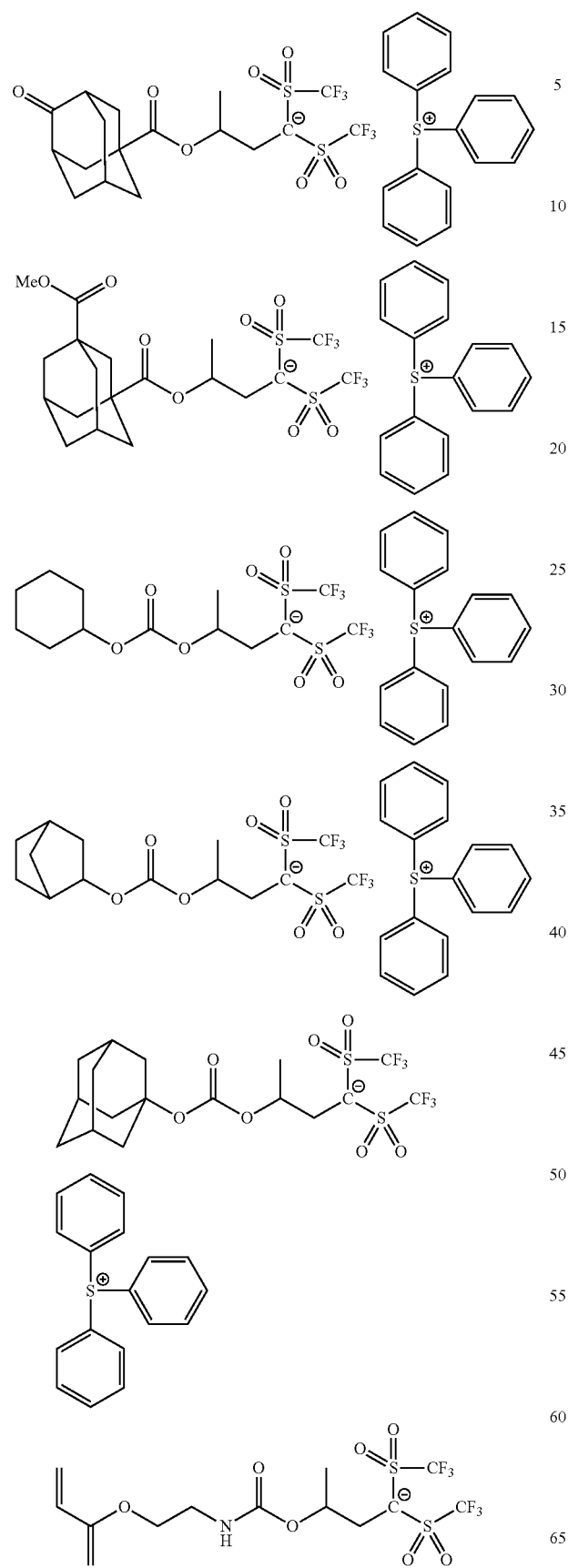
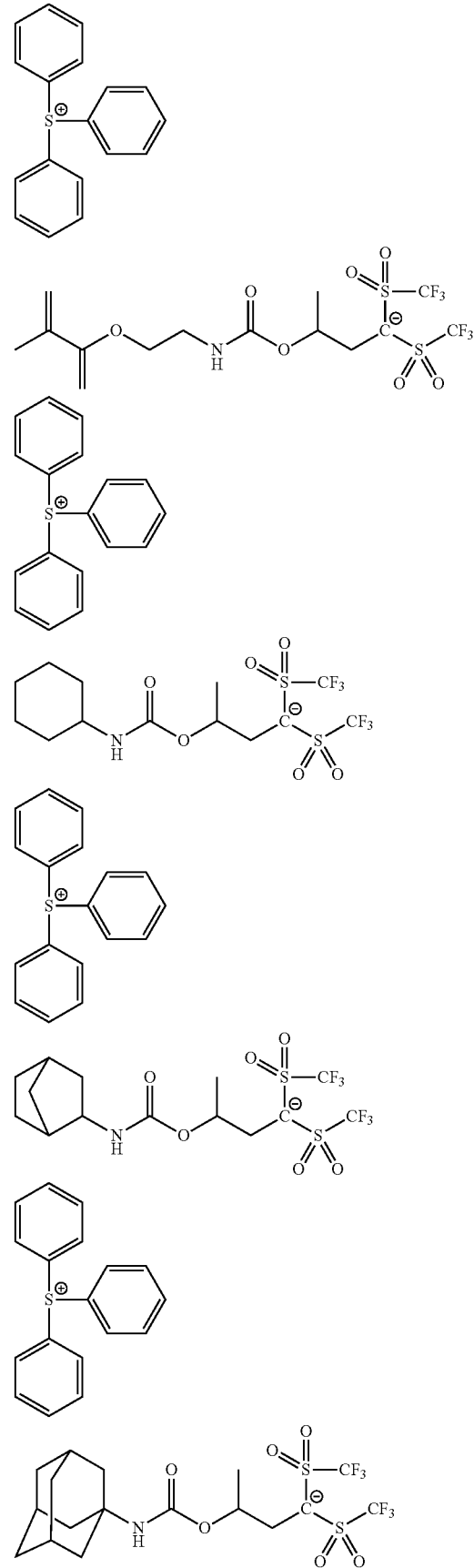

-continued

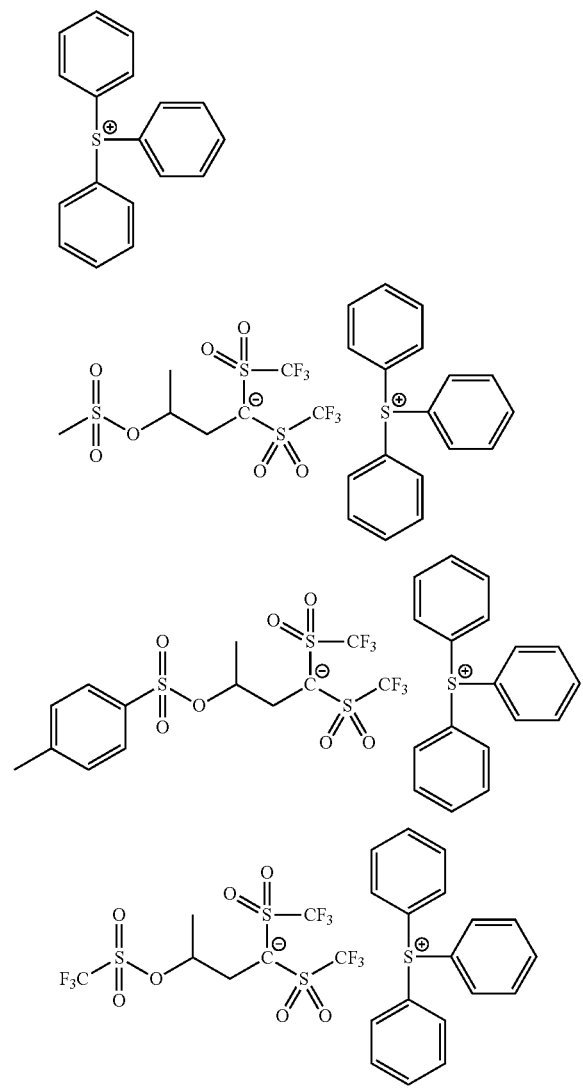

[Fluorine-Containing Alcohol]

A fluorine-containing alcohol, which is useful as a raw material for producing the acid having the fluorine-containing carbanion structure or the salt having the fluorine-containing carbanion structure of the present invention, is represented by the following general formula (10).

[Chemical Formula 52]

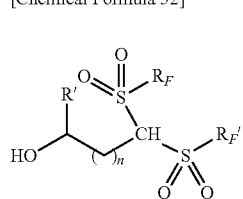

(10)

[In the above general formula (10), n, R', $R_F$, and $R_{F}'$ have the same meanings as those of n, R', $R_F$, and $R_{F}'$ in Fig. (1).]

Herein, the fluorine-containing alcohol represented by the general formula (10) can be exemplified by the followings.

[Chemical Formula 53]

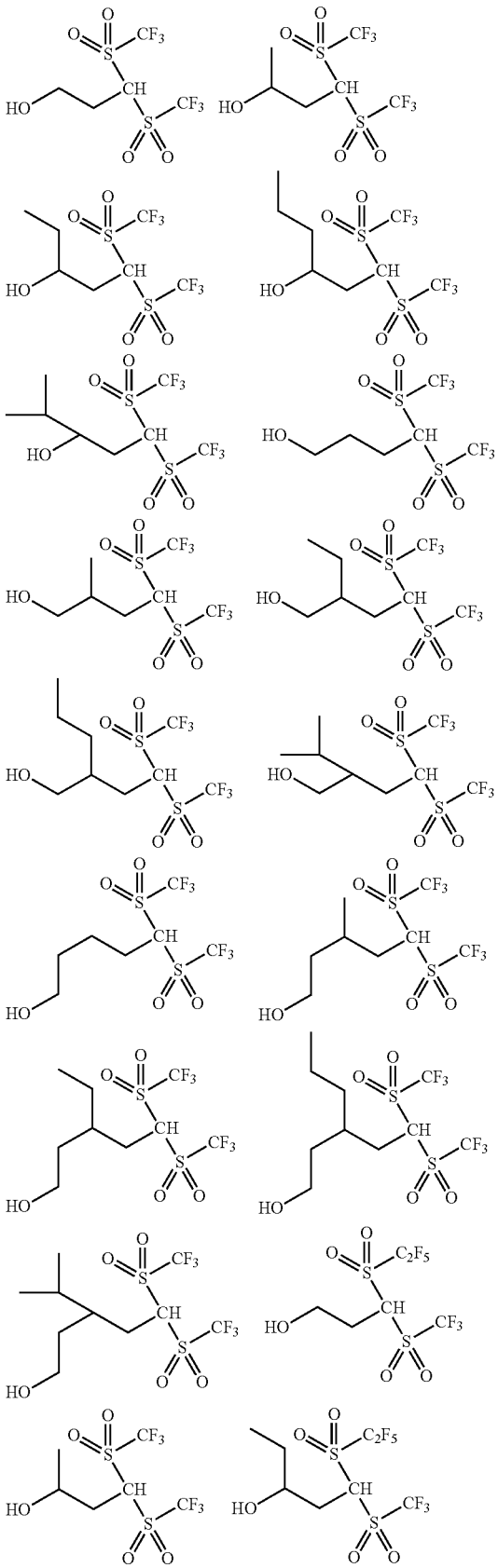

-continued
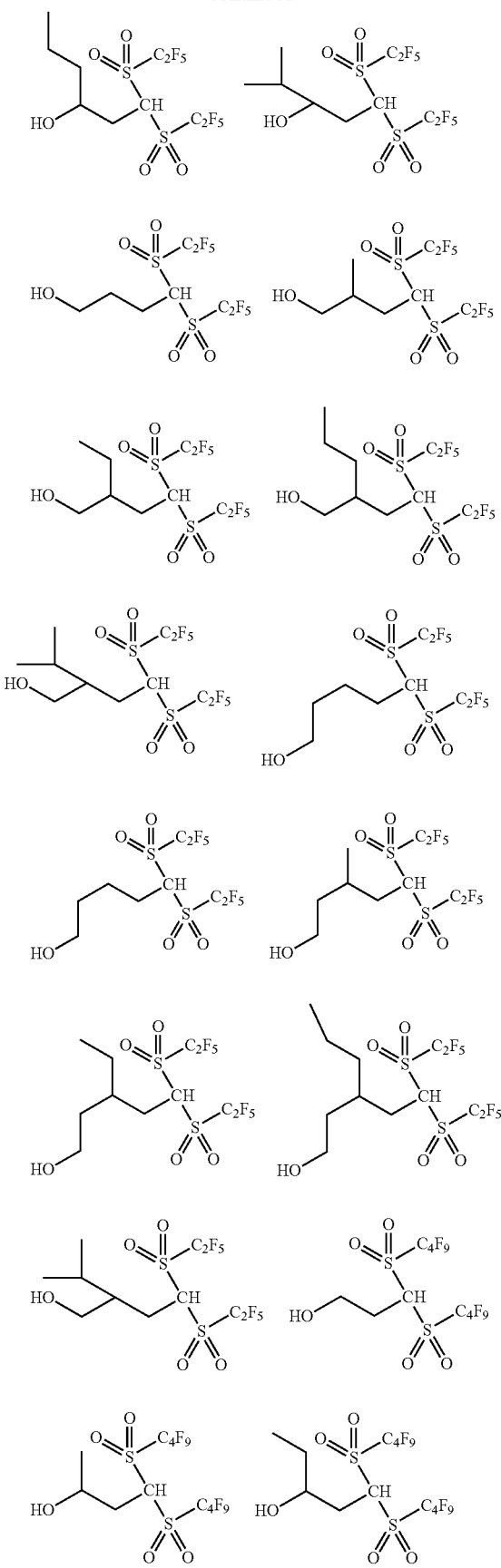
-continued
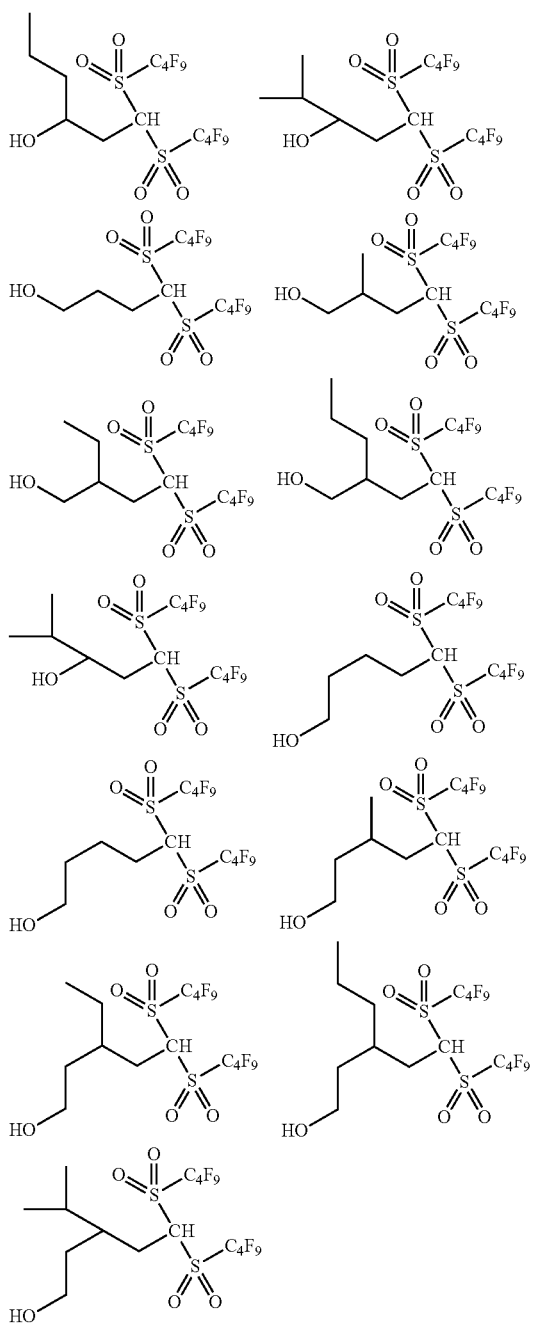
Of this, from the viewpoint of synthesis easiness, the following alcohols,
[Chemical Formula 54]
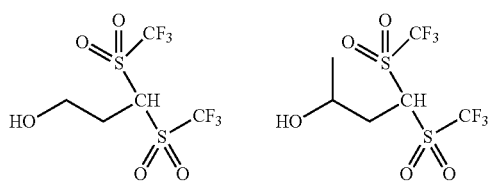

-continued

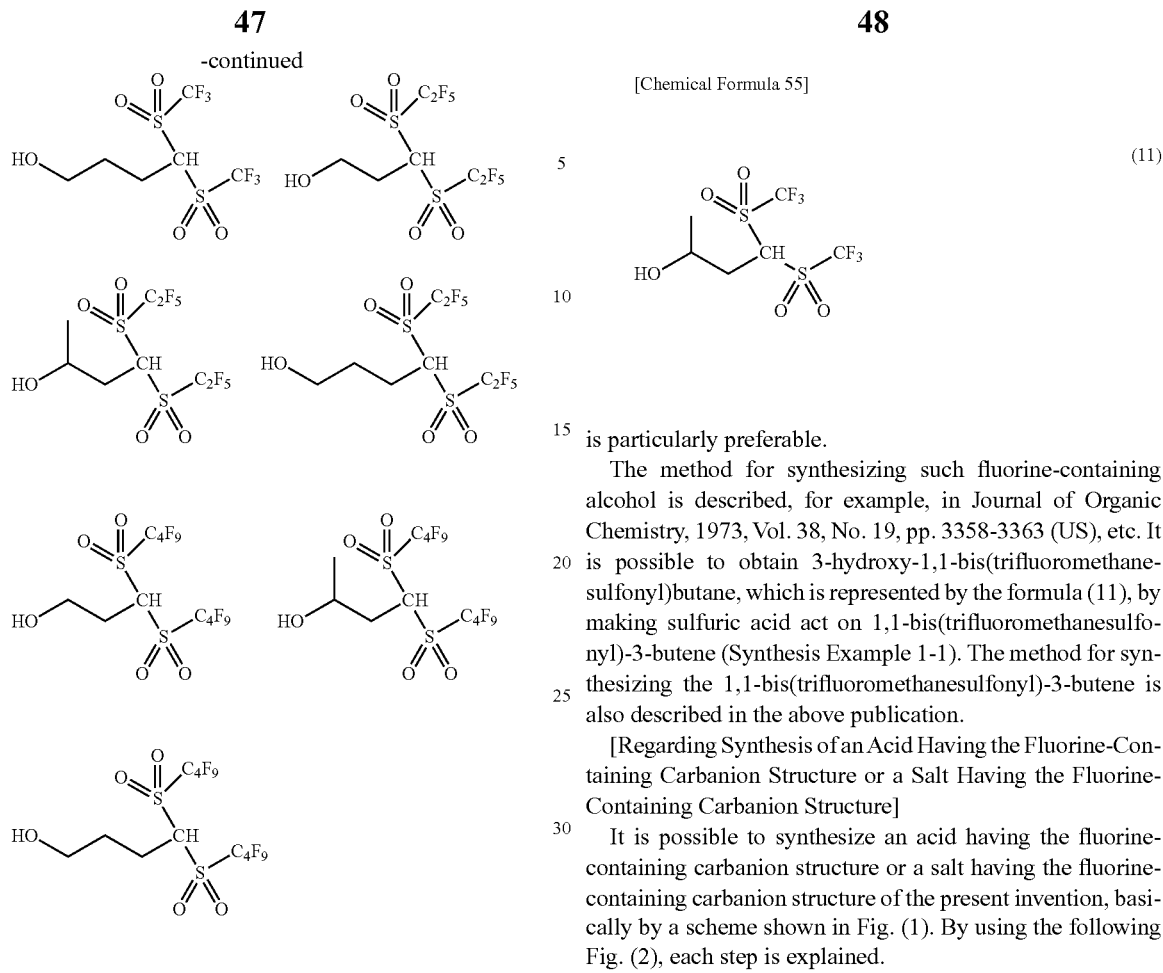

[Chemical Formula 55]

(11)

is particularly preferable.

The method for synthesizing such fluorine-containing alcohol is described, for example, in Journal of Organic Chemistry, 1973, Vol. 38, No. 19, pp. 3358-3363 (US), etc. It is possible to obtain 3-hydroxy-1,1-bis(trifluoromethanesulfonyl)butane, which is represented by the formula (11), by making sulfuric acid act on 1,1-bis(trifluoromethanesulfonyl)-3-butene (Synthesis Example 1-1). The method for synthesizing the 1,1-bis(trifluoromethanesulfonyl)-3-butene is also described in the above publication.

[Regarding Synthesis of an Acid Having the Fluorine-Containing Carbanion Structure or a Salt Having the Fluorine-Containing Carbanion Structure]

It is possible to synthesize an acid having the fluorine-containing carbanion structure or a salt having the fluorine-containing carbanion structure of the present invention, basically by a scheme shown in Fig. (1). By using the following Fig. (2), each step is explained.

[Chemical Formula 56]

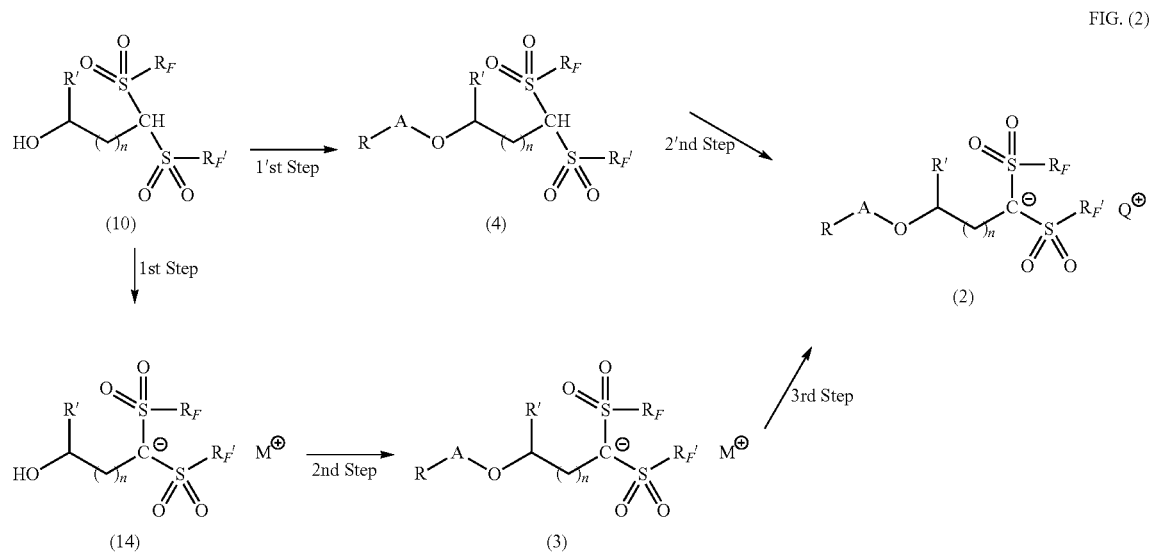

FIG. (2)

are preferable, and, of these, particularly 3-hydroxy-1,1-bis(trifluoromethanesulfonyl)butane represented by the following formula (11),

[In the above Fig. (2), n, R'R, A, $Q^+$, $M^+$, $R_F$ and $R_F'$ have the same meanings as those of n, R'R, A, $Q^+$, $M^+$, $R_F$ and $R_F'$ in Fig. (1).]

That is,

1st Step: a step of obtaining an acid salt having a fluorine-containing, hydroxy-containing, carbanion structure, which is represented by the general formula (14), by neutralizing an acidic fluorine-containing alcohol represented by the general formula (10), with a base containing at least M⁺.

1'st Step or 2nd Step: a step of converting the acidic fluorine-containing alcohol represented by the general formula (10) or a fluorine-containing hydroxyalkane salt represented by the general formula (14), which has been obtained by the 1st Step, into an acid having a fluorine-containing carbanion structure represented by the general formula (4) or a salt of acid having a fluorine-containing carbanion structure represented by the general formula (3).

Herein, the raw material to be used is different as follows, depending on the structure of A.

(1) In case that A is

[Chemical Formula 57]

it is possible to use as the raw material, for example, a carboxylic halide represented by the following general formula (15)

[Chemical Formula 58]

RCOX    (15)

[In the above general formula (15), R has the same meaning as that of R in Fig. (1). X represents a fluorine, chlorine, bromine or iodine.]
or a carboxylic anhydride represented by the following general formula (16)

[Chemical Formula 59]

(RCO)₂O    (16)

[In the above general formula (16), R has the same meaning as that of R in Fig. (1).] or the like.

(2) In case that A is

[Chemical Formula 60]

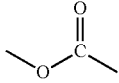

it is possible to use as the raw material, for example, an alkyl carbonate halide represented by the following general formula (17).

[Chemical Formula 61]

ROCOX    (17)

[In the above general formula (17), R has the same meaning as that of R in Fig. (1). X represents a fluorine, chlorine, bromine or iodine.]

(3) In case that A is

[Chemical Formula 62]

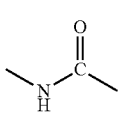

it is possible to use as the raw material, for example, an isocyanate represented by the following general formula (18).

[Chemical Formula 63]

RN=C=O    (18)

[In the above general formula (18), R has the same meaning as that of R in Fig. (1).]

(4) In case that A is

[Chemical Formula 64]

it is possible to use as the raw material, for example, an alkanesulfonic halide represented by the following general formula (19)

[Chemical Formula 65]

RSO₂X    (19)

[In the above general formula (19), R has the same meaning as that of R in Fig. (1). X represents a fluorine, chlorine, bromine or iodine.]
or a sulfonic anhydride represented by the following general formula (20)

[Chemical Formula 66]

(RSO₂)₂O    (20)

[In the above general formula (20), R has the same meaning as that of R in Fig. (1).] or the like.

2'nd Step or 3rd Step: a step of obtaining a salt formed of a fluorine-containing carbanion and an onium ion, which is represented by the general formula (2), by reacting a fluorine-containing alkane represented by the general formula (4), which has been obtained by the 1'st step, or a salt of an acid having a fluorine-containing carbanion structure, which is represented by the general formula (3) and has been obtained by the 2nd step, with a monovalent onium salt represented by the following general formula (21).

[Chemical Formula 67]

Q⁺X⁻    (21)

[In the above general formula (21), Q has the same meaning as that of Q in Fig. (1). X represents a fluorine, chlorine, bromine or iodine.]

By going through the above-mentioned steps, it is possible to synthesize an acid having a fluorine-containing carbanion structure or a salt having a fluorine-containing carbanion structure of the present invention.

[Photoacid Generator for Chemically Amplified Resist Materials]

As mentioned above, it is possible to produce an acid having a fluorine-containing carbanion structure represented by the general formula (4) of the present invention by irradiating a salt formed of a fluorine-containing carbanion and an onium ion, which is represented by the general formula (2), with ultraviolet rays, far-ultraviolet rays, extreme ultraviolet rays (EUV), electron beam, X-ray, excimer laser, γ-ray, or a high energy ray of synchrotron radiation irradiation ([Formula 1]).

[Chemical Formula 68]

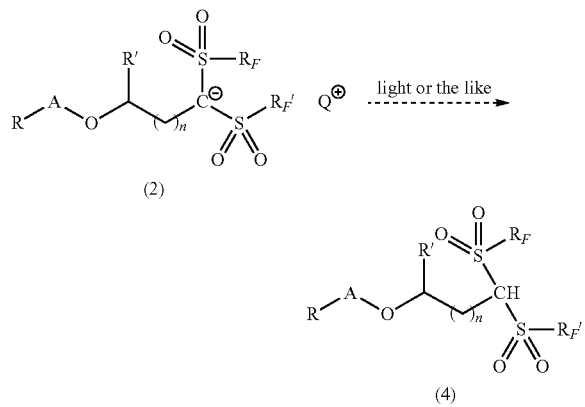

[In the above formula (1), n, R'R, A, Q$^+$, R$_F$ and R$_F$' have the same meanings as those of n, R'R, A, Q$^+$, R$_F$ and R$_F$' in Fig. (1).]

Therefore, it is possible to use a salt formed of a fluorine-containing carbanion and an onium ion, which is represented by the general formula (2), as a photoacid generator.

The photoacid generator of the present invention contains a salt formed of a fluorine-containing carbanion and an onium ion, which is represented by the above general formula (2), as an active component. By mixing the photoacid generator of the present invention with a resin (photosensitive resin) that changes solubility in an alkali developing solution by an action of acid, it is possible to form a photosensitive resin composition (resist material) for use. {In general, a simple substance (solid) of an onium salt of an acid having the above fluorine-containing carbanion structure is used as a photoacid generator alone or together with another photoacid generator by mixing in a photosensitive resin.}

As the polymer compound is exemplified, it can widely be applied to various photosensitive compositions, such as a positive-type resist, as the first example, in which the photoacid generator by the present invention turns into a strong acid (an acid having a fluorine-containing carbanion structure represented by the general formula (4)) after receiving a light or active energy ray irradiation, and in which a protective group of the polymer side chain is released by an action of the strong acid, and it changes into a polymer compound having an acidic unit that is soluble in the developing solution, such as carboxylic acid, phenol or hexafluoroalcohol, and a negative-type resist, as the second example, in which the photoacid generator by the present invention turns into a strong acid after receiving a light or electron beam irradiation, and in which an action of the strong acid makes a functional group of the polymer side chain react with a crosslinking agent that has previously been mixed, and it becomes insoluble in the developing solution.

Next, the resist material of the present invention is explained. The resist material of the present invention is one containing base resin, photoacid generator and solvent. Besides these, according to need, it is also possible to add an additive, such as a basic compound, a dissolution inhibitor, a crosslinking agent, etc.

The photoacid generator to be contained in the resist material of the present invention is as mentioned above. Its amount for the mixing is preferably in a range of 0.1-15 parts by weight relative to 100 parts by weight of the base resin. More preferably, it can be added in a range of 1-10 parts by weight.

[Base Resin]

Then, we explain a base resin added to a resist material according to the present invention. As the base resin, a repeating unit containing no aromatic substituent is used preferably. It is preferably a polymer obtained by polymerizing one kind of monomer selected from the group consisting of olefins, fluorine-containing olefins, acrylates, methacrylates, fluorine-containing acrylates, fluorine-containing methacrylates, norbornene compounds, fluorine-containing norbornene compounds, styrene-series compounds, fluorine-containing styrene-series compounds, vinyl ethers, and fluorine-containing vinyl ethers, or a copolymer obtained by copolymerizing at least two kinds of the above-mentioned monomers.

The olefins can be exemplified by ethylene, propylene, etc. The fluoroolefins can be exemplified by vinyl fluoride, vinylidene fluoride, trifluoroethylene, chlorotrifluoroethylene, tetrafluoroethylene, hexafluoropropylene, hexafluoroisobutene, etc.

Furthermore, the acrylates or methacrylates can be used without a particular limitation in terms of ester side chain. As they are exemplified by known compounds, it is possible to use alkyl esters of acrylic acid or methacrylic acid such as methyl acrylate or methacrylate, ethyl acrylate or methacrylate, n-propyl acrylate or methacrylate, isopropyl acrylate or methacrylate, n-butyl acrylate or methacrylate, isobutyl acrylate or methacrylate, n-hexyl acrylate or methacrylate, n-octyl acrylate or methacrylate, 2-ethylhexyl acrylate or methacrylate, lauryl acrylate or methacrylate, 2-hydroxyethyl acrylate or methacrylate, 2-hydroxypropyl acrylate or methacrylate, etc., acrylates or methacrylates containing ethylene glycol, propylene glycol or tetramethylene glycol group, unsaturated amides such as acrylamide, methacrylamide, N-methylol acrylamide, N-methylol methacrylamide, diacetone acrylamide, etc., vinyl silanes and acrylic or methacrylic esters containing acrylonitrile, methacrylonitrile or alkoxysilane, t-butyl acrylate or methacrylate, 3-oxocyclohexyl acrylate or methacrylate, adamantyl acrylate or methacrylate, alkyladamantyl acrylate or methacrylate, cyclohexyl acrylate or methacrylate, tricyclodecanylacrylate or methacrylate, an acrylate or methacrylate containing a ring structure such as lactone ring or norbornene ring, acrylic acid, methacrylic acid, etc. Furthermore, it is also possible to use the above-mentioned acrylate compounds containing a cyano group, and as analogous compounds maleic acid, fumaric acid, maleic anhydride, etc.

Furthermore, the fluorine-containing acrylate or fluorine-containing methacrylate is an acrylate or methacrylate having a group having a fluorine atom at α-position or ester moiety, and a cyano group may be introduced into α-position. For example, as the monomer having a fluorine-containing alkyl group introduced into α-position, there is preferably used a monomer in which α-position is provided with a trifluoromethyl group, trifluoroethyl group, nonafluoro-n-butyl group or the like.

On the other hand, they are acrylates or methacrylates, in which their ester moiety is a fluorine alkyl group that is a perfluoroalkyl group or fluoroalkyl group, or a unit in which a cyclic structure and fluorine are coexistent in the ester moiety, and which have a unit in which the cyclic structure has, for example, a fluorine-containing benzene ring, a fluorine-containing cyclopentane ring, a fluorine-containing cyclohexane ring, a fluorine-containing cycloheptane ring or the like, in which fluorine or trifluoromethyl group has been substituted therefor. Furthermore, it is also possible to use an acrylic or methacrylic acid ester of which ester moiety is a fluorine-containing t-butyl ester group, etc. Of such units, as particularly representative ones are exemplified in the form of monomer, it is possible to cite 2,2,2-trifluoroethyl acrylate, 2,2,3,3-tetrafluoropropyl acrylate, 1,1,1,3,3,3-hexafluoroisopropyl acrylate, heptafluoroisopropyl acrylate, 1,1-dihydroheptafluoro-n-butyl acrylate, 1,1,5-trihydrooctafluoro-n-pentyl acrylate, 1,1,2,2-tetrahydrotridecafluoro-n-octyl acrylate, 1,1,2,2-tetrahydroheptadecafluoro-n-decyl acrylate, 2,2,2-trifluoroethyl methacrylate, 2,2,3,3-tetrafluoropropyl methacrylate, 1,1,1,3,3,3-hexafluoroisopropyl methacrylate, heptafluoroisopropyl methacrylate, 1,1-dihydroheptafluoro-n-butyl methacrylate, 1,1,5-trihydrooctafluoro-n-pentyl methacrylate, 1,1,2,2-tetrahydrotridecafluoro-n-octyl methacrylate, 1,1,2,2-tetrahydroheptadecafluoro-n-decyl methacrylate, perfluorocyclohexylmethyl acrylate, perfluorocyclohexylmethyl methacrylate, etc.

The norbornene compounds and the fluorine-containing norbornene compounds are norbornene monomers having a single or plurality of nucleus structures, and these can be used without a particular limitation. Upon this, norbornene compounds are preferably used, that have been obtained by conducting Diels Alder addition reactions by using unsaturated compounds such as allyl alcohol, fluorine-containing allyl alcohol, acrylic acid, α-fluoroacrylic acid, methacrylic acid, and all of the acrylates or methacrylates and fluorine-containing acrylates or methacrylates mentioned in the present specification, and cyclopentadiene or cyclohexadiene.

Furthermore, it is also possible to use styrene-series compounds, fluorine-containing styrene-series compounds, vinyl ethers, fluorine-containing vinyl ethers, allyl ethers, vinyl esters, vinyl silanes, etc. Herein, as styrene-series compounds and fluorine-containing styrene-series compounds, it is possible to use, besides styrene, fluorinated styrene, hydroxystyrene, etc., hexafluoroacetone-added styrene-series compounds, styrene or hydroxystyrene having trifluoromethyl group substituted for hydrogen, the above-mentioned styrene or fluorine-containing styrene-series compound in which halogen, alkyl group or fluorine-containing alkyl group is attached to α-position, etc. On the other hand, it is also possible to use vinyl ethers, fluorine-containing vinyl ethers, allyl ethers, vinyl esters, etc. For example, they are alkyl vinyl ethers optionally containing methyl group, ethyl group, and hydroxy group such as hydroxyethyl group or hydroxybutyl group, and their hydrogen may partially or entirely be replaced with fluorine. Furthermore, it is also possible to use cyclohexyl vinyl ethers, cyclic-type vinyl ethers having hydrogen or carbonyl bond in their cyclic structure, and monomers in which hydrogen of those cyclic-type vinyl ethers has partially or entirely been replaced with fluorine. Furthermore, it is also possible to use allyl ethers, vinyl esters and vinyl silanes without a particular limitation, as long as they are publicly known compounds.

Of the above-mentioned base resins, particularly there is preferably used a base resin containing a repeating unit represented by the following general formula (5).

In the above general formula (5), $R^6$ represents a hydrogen atom, halogen atom, hydrocarbon group, or fluorine-containing alkyl group. $R^6$ is an alkyl group that is straight-chain or optionally branched, an alkyl group having a cyclic structure, an aromatic ring, or a complex substituent of them, and a part of that may be fluorinated. $R^7$ is a hydrogen atom, and a hydrocarbon group optionally branched, a fluorine-containing alkyl group, or a cyclic form having an aromatic or aliphatic ring, and may contain bond such as oxygen or carbonyl. Furthermore, s represents an integer of 1-2.

$R^5$ usable in the general formula (5) can be used without a particular limitation, as long as it is a hydrogen atom, halogen atom, hydrocarbon group, or fluorine-containing alkyl group. As preferable substituents are exemplarily shown, the halogen atom can be exemplified by fluorine, chlorine, bromine, etc. Furthermore, the hydrocarbon group can be exemplified by methyl group, ethyl group, propyl group, isopropyl group, butyl group, isobutyl group, sec-butyl group, tert-butyl group, cyclopentyl group, cyclohexyl group, phenyl group, benzyl group, phenethyl group, etc. Furthermore, the fluorine-containing alkyl group can be exemplified by those in which hydrogen atoms of the alkyl group have partially or entirely been replaced with halogen atom. However, the number of carbons in the case of the hydrocarbon group and the fluorine-containing alkyl group is preferably around 1-20. Furthermore, in view of polymerizability, the number of carbons of 1-4 is preferably used. In particular, as the fluorine-containing alkyl group is exemplified, it can be exemplified by trifluoromethyl group of —$CF_3$, trifluoroethyl group of —$CH_2CF_3$, 1,1,1,3,3,3-hexafluoroisopropyl group, heptafluoroisopropyl group, nonafluoro-n-butyl group of —$C_4F_9$, etc.

Furthermore, $R^6$ usable in the general formula (5) is an alkyl group that is straight-chain or optionally branched, an alkyl group having a cyclic structure, an aromatic ring, or a complex substituent of them, and a part of that may be fluorinated and may contain an unsaturated bond. Without limitation in structure, it is possible to use, for example, a straight-chain or branched alkylene group such as methylene, ethylene, isopropylene, t-butylene or the like, a cyclic structure containing cyclobutene, cyclohexane, norbornene, adamantane group or the like, phenyl group, etc. Of the structure represented by the general formula (5), as particularly preferable structures, repeating units represented by the following general formulas (6)-(8) can be shown as examples.

[Chemical Formula 69]

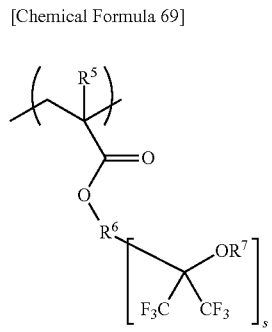

(5)

[Chemical Formula 70]

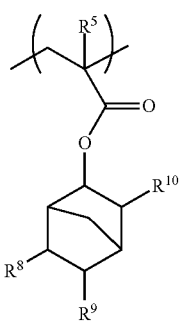

(6)

[Chemical Formula 71]

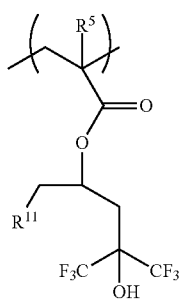

(7)

[Chemical Formula 72]

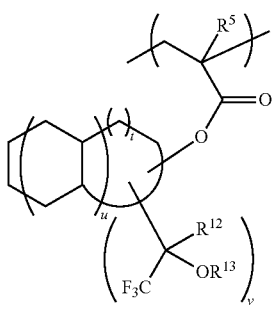

(8)

In the general formula (6), $R^5$ has the same meaning as that of W in the general formula (5). Any one of $R^8$, $R^9$ and $R^{10}$ is $CF_3C(CF_3)(OH)CH_2$— group, and the remaining two are hydrogen. In the general formula (7), $R^5$ has the same meaning as that of $R^5$ in the general formula (5). $R^{11}$ is a hydrogen atom, methyl group, ethyl group, n-propyl group, isopropyl group, n-butyl group, sec-butyl group, tert-butyl group, fluoromethyl group, difluoromethyl group, trifluoromethyl group, or perfluoroethyl group. In the general formula (8), $R^5$ has the same meaning as that of $R^5$ in the general formula (5). $R^{12}$ represents a methyl group or trifluoromethyl group. $R^{13}$ is a hydrogen atom, a $C_{1-25}$ straight-chain, branched or cyclic hydrocarbon group or a group containing an aromatic hydrocarbon group, and a part of that may contain fluorine atom, oxygen atom or carbonyl bond. u represents an arbitrary integer of 0-2. t and v represent arbitrary integers of 1-8, and satisfy v≤t+2. A $C_{1-25}$ straight-chain, branched or cyclic hydrocarbon group or an aromatic hydrocarbon group, which is usable as $R^{13}$ in the general formula (8), can be exemplified by methyl group, ethyl group, propyl group, isopropyl group, cyclopropyl group, n-propyl group, sec-butyl group, tert-butyl group, n-pentyl group, cyclopentyl group, sec-pentyl group, neopentyl group, hexyl group, cyclohexyl group, ethylhexyl group, norbornel group, adamantyl group, vinyl group, allyl group, butenyl group, pentenyl group, ethynyl group, phenyl group, benzyl group, 4-methoxybenzyl group, etc., and those in which the above functional groups have partially or entirely been replaced with fluorine atom are also fine. Furthermore, as those having oxygen atom, it is possible to mention alkoxycarbonyl group, acetal group, acyl group, etc. The alkoxycarbonyl group can be exemplified by tert-butoxycarbonyl group, tert-amyloxycarbonyl group, methoxycarbonyl group, ethoxycarbonyl group, i-propoxycarbonyl group, etc. As the acetal group, it is possible to mention chain-like ethers of methoxymethyl group, methoxyethoxymethyl group, ethoxyethyl group, butoxyethyl group, cyclohexyloxyethyl group, benzyloxyethyl group, phenethyloxyethyl group, ethoxypropyl group, benzyloxypropyl group, phenethyloxypropyl group, ethoxybutyl group and ethoxyisobutyl group, and cyclic ethers such as tetrahydrofuranyl group and tetrahydropyranyl group. As the acyl group, it is possible to mention acetyl group, propionyl group, butyryl group, heptanoyl group, hexanoyl group, valeryl group, pivaloyl group, isovaleryl group, lauryloyl group, myristoyl group, palmytoyl group, stearoyl group, oxalyl group, malonyl group, succinyl group, glutaryl group, adipoyl group, piperoyl group, suberoyl group, azelaoyl group, sebacoyl group, acryloyl group, propioloyl group, methacryloyl group, crotonoyl group, oleoyl group, maleoyl group, fumaroyl group, mesaconoyl group, campholoyl group, benzoyl group, phthaloyl group, isophthaloyl group, terephthaloyl group, naphthoyl group, toluoyl group, hydratoropoyl group, atoropoyl group, cinnamoyl group, furoyl group, thenoyl group, nicotinoyl group, isonicotinoyl group, etc. Furthermore, it is also possible to use those in which hydrogen atoms of the above substituents have partially or entirely been replaced with fluorine atom.

On the other hand, besides a base resin containing a repeating unit represented by the above-mentioned general formula (5), there is also preferably used a base resin containing a repeating unit represented by the following general formula (9).

[Chemical Formula 73]

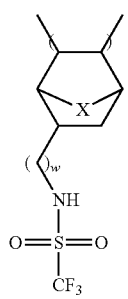

(9)

In the above general formula (9), X represents any of —$CH_2$—, —O—, and —S—. w represents an integer of 2-6.

Furthermore, besides repeating units represented by the above-mentioned general formula (5) and general formula (9), there is also preferably used a base resin containing a repeating unit represented by the following general formula (23).

[Chemical Formula 74]

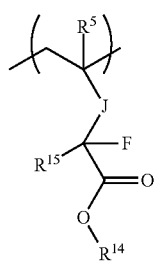

(23)

In the above general formula (23), $R^5$ has the same meaning as that of $R^5$ in the general formula (5).

$R^{15}$ is a fluorine atom or fluorine-containing alkyl group. As such fluorine-containing alkyl group, although it is not particularly limited, it is one having a carbon number of 1-12. One having a carbon number of 1-3 is preferable. It is possible to mention trifluoromethyl group, pentafluoroethyl group, 2,2,2-trifluoroethyl group, n-heptafluoropropyl group, 2,2,3,3,3-pentafluoropropyl group, 3,3,3-trifluoropropyl group, hexafluoroisopropyl group, etc. $R^{15}$ is more preferably a fluorine atom or trifluoromethyl group.

$R^{14}$ is a hydrogen atom, a substituted or unsubstituted $C_{1-25}$ straight-chain, branched or cyclic aliphatic hydrocarbon group, or a substituted or unsubstituted $C_{6-25}$ aromatic hydrocarbon group, and a part of that may contain fluorine atom, ether bond or carbonyl group.

A $C_{1-25}$ straight-chain, branched or cyclic hydrocarbon group or an aromatic hydrocarbon group, which is usable as $R^{14}$, can be exemplified by methyl group, ethyl group, propyl group, isopropyl group, cyclopropyl group, n-propyl group, sec-butyl group, tert-butyl group, n-pentyl group, cyclopentyl group, sec-pentyl group, neopentyl group, hexyl group, cyclohexyl group, ethylhexyl group, norbornel group, adamantyl group, vinyl group, allyl group, butenyl group, pentenyl group, ethynyl group, phenyl group, benzyl group, 4-methoxybenzyl group, etc., and those in which the above functional groups have partially or entirely been replaced with fluorine atom are also fine. Furthermore, as those having oxygen atom, it is possible to mention alkoxycarbonyl group, acetal group, acyl group, etc. The alkoxycarbonyl group can be exemplified by tert-butoxycarbonyl group, tert-amyloxycarbonyl group, methoxycarbonyl group, ethoxycarbonyl group, i-propoxycarbonyl group, etc. As the acetal group, it is possible to mention chain-like ethers of methoxymethyl group, methoxyethoxymethyl group, ethoxyethyl group, butoxyethyl group, cyclohexyloxyethyl group, benzyloxyethyl group, phenethyloxyethyl group, ethoxypropyl group, benzyloxypropyl group, phenethyloxypropyl group, ethoxybutyl group and ethoxyisobutyl group, and cyclic ethers such as tetrahydrofuranyl group and tetrahydropyranyl group. As the acyl group, it is possible to mention acetyl group, propionyl group, butyryl group, heptanoyl group, hexanoyl group, valeryl group, pivaloyl group, isovaleryl group, lauryloyl group, myristoyl group, palmytoyl group, stearoyl group, oxalyl group, malonyl group, succinyl group, glutaryl group, adipoyl group, piperoyl group, suberoyl group, azelaoyl group, sebacoyl group, acryloyl group, propioloyl group, methacryloyl group, crotonoyl group, oleoyl group, maleoyl group, fumaroyl group, mesaconoyl group, campholoyl group, benzoyl group, phthaloyl group, isophthaloyl group, terephthaloyl group, naphthoyl group, toluoyl group, hydratoropoyl group, atoropoyl group, cinnamoyl group, furoyl group, thenoyl group, nicotinoyl group, isonicotinoyl group, etc. Furthermore, it is also possible to use those in which hydrogen atoms of the above substituents have partially or entirely been replaced with fluorine atom.

The linking group J in the general formula (23) is a bivalent linking group formed of a single one selected from the group consisting of a single bond, —$(CR^{16}R^{17})$n- (n represents an integer of 1-10), —O—, —C(=O—O)—C(=O)O— or —O—C(=O)—, thioether group, ester group, amide group, sulfonamide group, urethane group or urea group, or formed of a combination of these.

Of these, as the linking group J obtained by the combination,
—$(CR^{16}R^{17})_m$—C(=O)—O—$(CR^{16}R^{17})_n$—
—$(CR^{16}R^{17})_m$—O—$(CR^{161}R^{17})_n$—
and the like can be mentioned. Here, m and n represent integers of 0-10, m is preferably 0, and n is preferably 1.

Of this, a monovalent organic group represented by $R^{16}$ or $R^{17}$ of each substituted methylene group is not particularly limited, but it is a hydrogen atom, hydroxy group, or a $C_1$-$C_{30}$ monovalent organic group selected from alkyl groups, alicyclic hydrocarbon groups, substituted alkyl groups, alkoxy groups, aryl groups, and condensed polycyclic aromatic groups. These monovalent organic groups can have fluorine atom, oxygen atom, sulfur atom, nitrogen atom, or carbon-carbon double bond. Both of them may be the same or different. Furthermore, $R^{16}$ and $R^{17}$ may be combined to form a ring, and this ring is preferably an alicyclic hydrocarbon group.

The alkyl group is one having a carbon number of 1-30, and one having a carbon number of 1-12 is preferable. For example, it is possible to mention methyl group, ethyl group, n-propyl group, i-propyl group, n-butyl group, 1-methylpropyl group, 2-methylpropyl group, tert-butyl group, n-pentyl group, i-pentyl group, 1,1-dimethylpropyl group, 1-methylbutyl group, 1,1-dimethylbutyl group, n-hexyl group, n-heptyl group, i-hexyl group, n-octyl group, i-octyl group, 2-ethylhexyl group, n-nonyl group, n-decyl group, n-undecyl group, n-dodecyl group, etc. It is possible to mention methyl group, ethyl group, n-propyl group, i-propyl group, etc. as particularly preferable ones. As substituents of the substituted alkyl groups, it is possible to mention $C_1$-$C_4$ alkoxy group, halogen atom (fluorine atom, chlorine atom, bromine atom, or iodine atom), acyl group, acyloxy group, cyano group, hydroxy group, carboxy group, alkoxycarbonyl group, nitro group, etc., for one or at least two of hydrogen atoms possessed by the substituents. Those replaced with fluorine atoms are preferable. Specifically, it is possible to mention trifluoromethyl group, pentafluoroethyl group, 2,2,2-trifluoroethyl group, n-heptafluoropropyl group, 2,2,3,3,3-pentafluoropropyl group, 3,3,3-trifluoropropyl group, and hexafluoroisopropyl group.

As the alkoxy groups, it is possible to mention those having a carbon number of 1-4, such as methoxy group, ethoxy group, propoxy group, butoxy group, etc.

The aryl groups are those having a carbon number of 1-30. As a monocyclic group, one having a ring carbon number of 3-12 is preferable, and one having a ring carbon number of 3-6 is more preferable. It is possible to mention, for example, phenyl group, biphenyl group, terphenyl group, o-tolyl group, m-tolyl group, p-tolyl group, p-hydroxyphenyl group, p-methoxyphenyl group, mesityl group, o-cumenyl group, 2,3-xylyl group, 2,4-xylyl group, 2,5-xylyl group, 2,6-xylyl group, 3,4-xylyl group, 3,5-xylyl group, o-fluorophenyl group, m-fluorophenyl group, p-fluorophenyl group, o-trifluoromethylphenyl group, m-trifluoromethylphenyl group, p-trifluoromethylphenyl group, 2,3-bistrifluoromethyl group, 2,4-bistrifluoromethyl group, 2,5-bistrifluoromethyl group, 2,6-bistrifluoromethyl group, 3,4-bistrifluoromethyl group, 3,5-bistrifluoromethyl group, p-chlorophenyl group, p-bromophenyl group, p-iodophenyl group, etc.

As $C_1$-$C_{30}$ condensed polycyclic aromatic ring groups, it is possible to mention monovalent organic groups containing, as a condensed polycyclic aromatic ring, pentalene, indene, naphthalene, azlene, heptalene, biphenylene, indacene, acenaphthylene, fluorene, phenarene, phenanthrene, anthracene, fluoranthene, acephenanthrylene, aceanthrylene, triphenylene, pyrene, chrysene, naphtacene, picene, perylene, pentaphene, pentacene, tetraphenylene, hexaphene, hexacene, rubicene, coronene, trinaphthylene, heptaphene, heptacene, pyranthrene, ovalene, etc. As a preferable one, it is possible to mention one in which one or at least two hydrogen atoms of these have been replaced with fluorine atom, a $C_1$-$C_4$ alkyl group or fluorine-containing alkyl group.

As a monocyclic or polycyclic, heterocyclic group having a ring atom number of 3-25, it is possible to mention pyridyl group, furyl group, thienyl group, pyranyl group, pyrrolyl group, thiantrenyl group, pyrazolyl group, isothiazolyl group, isoxazolyl group, pyrazinyl group, pyrimidinyl group, pyridadinyl group, tetrahydropyranyl group, tetrahydrofuranyl group, tetrahydrothiopyranyl group, tetrahydrothiofuranyl group, 3-tetrahydrothiophen-1,1-dioxide group, and heterocyclic groups in which one or at least two hydrogen atoms of the atoms constituting these rings have been replaced with alkyl group, alicyclic hydrocarbon group, aryl group or heterocyclic group. Of these, one having a monocyclic or polycyclic ether ring or lactone ring is preferable.

An alicyclic hydrocarbon group in $R^{16}$ and $R^{17}$ constituting the linking group J or an alicyclic hydrocarbon group formed by containing a carbon atom to which they are attached may be monocyclic or polycyclic. Specifically, it is possible to mention a group having a monocyclo, bicyclo, tricyclo, tetracyclo structure, etc. having a carbon number of at least 3. The carbon number is preferably 3-30, and particularly a carbon number of 3-25 is preferable. These alicyclic hydrocarbon groups may have substituents.

The monocyclic group is preferably one having a ring carbon number of 3-12 and is more preferably one having a ring carbon number of 3-7. It is possible to mention, for example, as preferable ones, cyclopropyl group, cyclobutyl group, cyclopentyl group, cyclohexyl group, cycloheptyl group, cyclooctyl group, cyclodecanyl group, cyclododecanyl group, tricyclodecanyl group and 4-tert-butylcyclohexyl group. Furthermore, as polycyclic group, it is possible to mention adamantyl group, noradamantyl group, decaline residue, tricyclodecanyl group, tetracyclododecanyl group, norbornyl group, cedrol group, and the like of a ring carbon number of 7-15. The alicyclic hydrocarbon group may be a spiro ring, and a spiro ring having a carbon number of 3-6 is preferable. Preferably, they are adamantyl group, decaline residue, norbornyl group, cedrol group, cyclohexyl group, cycloheptyl group, cyclooctyl group, cyclodecanyl group, cyclododecanyl group, and tricyclodecanyl group, etc. It is possible to mention one in which one or at least two of hydrogen atoms of the ring carbon or linking group of these organic groups have respectively independently been replaced with the above-mentioned $C_1$-$C_{25}$ alkyl group or substituted alkyl group, hydroxy group, alkoxy group, carboxyl group, alkoxycarbonyl group, or one in which one or at least two hydrogen atoms of those have been replaced with fluorine atoms or trifluoromethyl groups.

Herein, the alkyl group is preferably methyl group, ethyl group, propyl group, isopropyl group, butyl group, etc. (It is referred to as "a lower alkyl group". It is the same in the present specification.). More preferably, it is an alkyl group selected from the group consisting of methyl group, ethyl group, propyl group and isopropyl group. As the substituent of the substituted alkyl group, it is possible to mention hydroxy group, halogen atom, and alkoxy group. As the alkoxy group, it is possible to mention one having a carbon number of 1-4, such as methoxy group, ethoxy group, propoxy group, butoxy group, etc. As the alkoxycarbonyl group, it is possible to mention methoxycarbonyl group, ethoxycarbonyl group, and isopropoxycarbonyl group.

As the linking group J, specifically,
—O—
—C(═O)—O—
—CH$_2$—O—
—O—CH$_2$—
—CH$_2$—C(═O)—O—
—C(═O)—O—CH$_2$—
—CH$_2$—O—CH$_2$—
—CH$_2$—C(═O)—O—CH$_2$—
and the like, and —C(═O)—O—CR$^{16}$R$^{17}$—, in which each of $R^{16}$ and $R^{17}$ is independently a hydrogen atom, fluorine atom, alkyl group, substituted alkyl group, or alicyclic hydrocarbon group, can be mentioned as preferable ones. Of these, it is possible to mention one in which each of $R^{16}$ and $R^{17}$ is independently a hydrogen atom or lower alkyl group, as a more preferable one.

As molecular weight of the base resin, a polymer compound having the above-mentioned repeating unit and a weight average molecular weight of 1,000-1,000,000 is preferable. In case that molecular weight is less than this, it is not sufficient in terms of mechanical strength and film forming property. In case that molecular weight is greater than this, it is not preferable in terms of solubility in solvent and formability. Furthermore, it is also possible to blend at least of the above polymers.

To make the resist material into a chemically amplified positive type, there is used a base resin that is insoluble or poorly soluble in a developing solution (normally, an alkali developing solution) and becomes soluble in the developing solution by acid.

A base resin containing a repeating unit having an acid-labile group is a polymer compound prepared by mixing a polymerizable monomer having an acid-labile group with a polymerizable monomer that generates the above-mentioned repeating unit and then conducting copolymerization, or one in which a part of the base resin containing the above-mentioned repeating unit has been converted into an acid-labile group. Examples of the acid-labile group can be used without a particular limitation, as long as they are groups that leave by the effect of the above-mentioned photoacid generator. As specific examples are mentioned, it is possible to mention alkykoxycarbonyl group, acetal group, silyl group, acyl group, etc. The alkoxycarbonyl group can be exemplified by tert-butoxycarbonyl group, tert-amyloxycarbonyl group, methoxycarbonyl group, ethoxycarbonyl group, i-propoxycarbonyl group, etc. As the acetal group, it is possible to mention methoxymethyl group, ethoxyethyl group, butoxyethyl group, cyclohexyloxyethyl group, benzyloxyethyl group, phenethyloxyethyl group, ethoxypropyl group, benzyloxypropyl group, phenethyloxypropyl group, ethoxybutyl group, ethoxyisobutyl group, etc. It is also possible to use an acetal group in which a vinyl ether has been added to a hydroxy group. As the silyl group, it is possible to mention, for example, trimethylsilyl group, ethyldimethylsilyl group, methyldiethylsilyl group, triethylsilyl group, i-propyldimethylsilyl group, methyldi-i-propylsilyl group, tri-i-propylsilyl group, t-butyldimethylsilyl group, methyldi-t-butylsilyl group, tri-t-butylsilyl group, phenyldimethylsilyl group, methyldiphenylsilyl group, triphenylsilyl group, etc. As the acyl group, it is possible to mention acetyl group, propionyl group, butyryl group, heptanoyl group, hexanoyl group, valeryl group, pivaloyl group, isovaleryl group, lauryloyl group, myristoyl group, palmytoyl group, stearoyl group, oxalyl group, malonyl group, succinyl group, glutaryl group, adipoyl group, piperoyl group, suberoyl group, azelaoyl group, sebacoyl group, acryloyl group, propioloyl group, methacryloyl group, crotonoyl group, oleoyl group, maleoyl group, fumaroyl group, mesaconoyl group, campholoyl group, benzoyl group, phthaloyl group, isophthaloyl group, terephthaloyl group, naphthoyl group, toluoyl group, hydratoropoyl group, atoropoyl group, cinnamoyl group, furoyl group, thenoyl group, nicotinoyl group, isonicotinoyl group, etc. Furthermore, it is also possible to use those in which hydrogen atoms of these acid-labile groups have partially or entirely been replaced with fluorine atom.

[Solvent]

As an organic solvent to be added to the resist material of the present invention, any will do as long as it is an organic solvent in which base resin, acid generator, other additives, etc. are soluble. As such organic solvent, it is possible to use ketones such as acetone, methyl ethyl ketone, cyclohexanone, methyl isoamyl ketone and 2-heptanone; polyhydric alcohols such as ethylene glycol, ethylene glycol monoacetate, diethylene glycol, diethylene glycol monoacetate, propylene glycol, propylene glycol monoacetate, dipropylene glycol, or monomethyl ether, monoethyl ether, monopropyl ether, monobutyl ether or monophenyl ether of dipropylene glycol monoacetate, and their derivatives; cyclic ethers such as dioxane; esters such as methyl lactate, ethyl lactate, methyl acetate, ethyl acetate, butyl acetate, methyl pyruvate, ethyl pyruvate, methyl methoxypropionate, and ethyl ethoxypropionate; aromatic solvents such as xylene and toluene; fluorine-series solvents such as freon, alternative freon, perfluoro compounds, and hexafluoroisopropyl alcohol; and terpene-based petroleum naphtha solvents and paraffinic solvents, which are high-boiling-point, weak solvents, for the purpose of increasing applicability. These may be used singly or in a mixture of at least two kinds.

Usage of the organic solvent is 200-1,000 parts by weight relative to 100 parts by weight of the base resin, and particularly 400-800 parts by weight is preferable.

[Pattern Forming Method]

The resist material of the present invention can preferably be used for pattern forming by going through each step of the step of applying the resist material onto a substrate, the step of exposing it with a high-energy ray of a wavelength of 300 nm or less through a photomask after heating treatment, and the step of developing it by using developing solution, after heating treatment according to need.

As usage of the resist material of the present invention, it is possible to use a resist pattern forming process of a conventional photoresist technique. That is, firstly the resist material is applied on a substrate such as silicon wafer by using a spinner or the like. A photosensitive layer is formed by drying. This is irradiated with a high-energy ray through a desired mask pattern by an exposure device or the like, followed by heating. Then, this is subjected to a developing treatment by using a developing solution, for example, an alkali aqueous solution such as 0.1-10 weight % tetramethylammonium hydroxide aqueous solution. It is possible by this forming method to obtain a pattern conforming to the mask pattern. Furthermore, according to desire, it is possible to contain additives that are miscible with the resist material, for example, various additives such as additional resins, quencher, plasticizer, stabilizer, coloring agent, surfactant, tackifier, leveling agent, defoaming agent, compatibility enhancing agent, adhesion enhancing agent, antioxidant, etc.

A high-energy ray of a wavelength of 300 nm or less used in the present invention is not particularly limited. Ultraviolet rays, far-ultraviolet rays, extreme ultraviolet rays (EUV), electron beam, X-ray, excimer laser, γ-ray, or a high energy ray of synchrotron radiation irradiation can be shown as examples. In particular, in the case of conducting a fine processing, it is effective to use an exposure device equipped with a source for generating a short-wavelength high-energy ray such as ArF excimer laser, KrF excimer laser, or EUV. It is effective to use an immersion exposure device that makes it possible to conduct a more efficient fine processing in numerical aperture and effective wavelength by using a medium, such as water or a fluorine-based solvent, into which the high-energy ray to be used has a less absorption, at a part of the optical path. The present resist material is preferable in the case of use in this device.

Of the above-mentioned pattern forming methods, an immersion lithography, in which an ArF excimer laser of 193 nm in wavelength is used and in which water is inserted between wafer and projector lens, is one of particularly preferable modes.

EXAMPLES

In the following, the present invention is specifically explained by showing synthesis examples, examples, reference examples and comparative examples, but the present invention is not limited by the following examples.

Production of an acid having a fluorine-containing carbanion structure or a salt having a fluorine-containing carbanion structure Synthesis Example 1-1

3-hydroxy-1,1-bis(trifluoromethanesulfonyl)butane

[Chemical Formula 75]

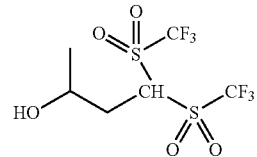

Under a nitrogen atmosphere, a four-necked 300 ml flask equipped with a reflux condenser was charged with 37.4 g (0.374 mol) of 98% concentrated sulfuric acid. Then, the reactor was immersed in a water bath, and 79.8 g (0.249 mol) of 1,1-bis(trifluoromethanesulfonyl)-3-butene was added dropwise into the reactor at an inside temperature of 18-25° C. After terminating the dropping, stirring was continued for 1 hr at the temperature as it was. Then, stirring was conducted at 35° C. for 4 hr, thereby completing the reaction. Monitoring of the reaction was conducted by $^{19}$F-NMR.

After confirming the formation of a sulfate, the reactor was cooled, and 79.8 g (100 wt %) of water was added dropwise. By adjusting the dropping rate, the inside temperature was controlled at about 30° C. Then, the reactor was heated to 90° C., and stirring was conducted for 1 hr. After terminating heating, the reactor was cooled, and an extraction operation was conducted two times by using 80 g of toluene. The extracted organic layers were combined, followed by drying with anhydrous magnesium sulfate and then isolating the target compound by distillation under reduced pressure. The target compound was distilled out at 91-94° C. under a reduced pressure of 400 Pa to obtain 67.6 g (yield 80.2%).

Properties of
3-hydroxy-1,1-bis(trifluoromethanesulfonyl)butane $^1$H NMR (measurement solvent: deuteriochloroform, standard substance: tetramethylsilane); δ=5.51 (dd, 1H), 4.08 (m, 1H), 2.66 (ddd, 1H), 2.38 (dd, 1H), 1.87 (s, 1H), 1.35 (d, 3H)

$^{19}$F NMR (measurement solvent: deuteriochloroform, standard substance: tetramethylsilane); δ=−72.7 (s, 3F), −73.9 (s, 3F)

Synthesis Example 1-2

Production of 3-hydroxy-1,1-bis(trifluoromethanesulfonyl)butane sodium salt

[Chemical Formula 76]

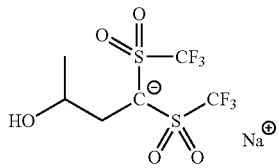

A glass flask was charged with 2 g (0.0059 mol) of 3-hydroxy-1,1-bis(trifluoromethanesulfonyl)butane and 20 g of water, followed by stirring. Then, 0.52 g (0.0062 mol) of 48% sodium hydroxide aqueous solution was added dropwise. After terminating the dropping, stirring was continued at room temperature for 1 hr. Then, solvent was distilled out of the reaction liquid with an evaporator, thereby obtaining 2.26 g (yield 91%, purity 86%) of 3-hydroxy-1,1-bis(trifluoromethanesulfonyl)butane sodium salt as a white solid.

Properties of 3-hydroxy-1,1-bis(trifluoromethanesulfonyl)butane sodium salt $^1$H NMR (measurement solvent: deuterated DMSO, standard substance: tetramethylsilane); δ-=3.63 (m, 1H), 3.53 (brs, 1H), 2.45 (brs, 1H), 2.07 (brs, 1H), 1.01 (d, 3H)
$^{19}$F NMR (measurement solvent: deuterated DMSO, standard substance: tetramethylsilane); δ=−77.9 (brs, 6F)

Synthesis Example 1-3

Production of 3-methacryloxy-1,1-bis(trifluoromethanesulfonyl)butane triphenylsulfonium salt

[Chemical Formula 77]

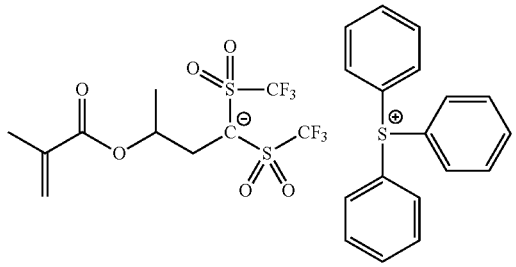

A glass flask was charged with 10 g (0.029 mol) of 3-hydroxy-1,1-bis(trifluoromethanesulfonyl)butane, 40 g of chloroform, 0.01 g (0.1 wt %) of 2,2'-methylene-bis(4-methyl-6-tert-butylphenol) (NONFLEX MBP made by Seiko Chemical Co., Ltd.), and 0.09 g (0.0009 mol) of methanesulfonic acid, followed by stirring. Then, 5.5 g (0.035 mol) of methacrylic anhydride was added dropwise. After terminating the dropping, stirring was conducted at 55° C. for 4 hr. Then, the inside temperature was cooled until room temperature, and 15 g of water was added to the reaction liquid. Then, a 40 ml-water solution of 10 g (0.033 mol) of triphenylsulfonium chloride was added dropwise. After terminating the dropping, stirring was continued at room temperature for 1 hr. Then, the organic layer of the reaction liquid was washed five times with 40 ml of water, followed by distilling solvent off with an evaporator. The obtained liquid of a pale yellow color was further washed three times with 40 ml of diethyl ether, followed by drying with a vacuum pump, thereby obtaining 11.5 g (yield 59%, purity 95%) of 3-methacryloxy-1,1-bis(trifluoromethanesulfonyl)butane triphenylsulfonium salt as a pale yellow color liquid.

Properties of 3-methacryloxy-1,1-bis(trifluoromethanesulfonyl)butane triphenylsulfonium salt $^1$H NMR (measurement solvent: deuteriochloroform, standard substance: tetramethylsilane): δ=6.05 (s, 1H), 5.40 (s, 1H), 5.01 (q, 1H), 2.73 (brs, 1H), 2.53 (brs, 1H), 1.23 (d, 3H)
$^{19}$F NMR (measurement solvent: deuteriochloroform, standard substance: tetramethylsilane); δ=−79.1 (s, 6F)

Synthesis Example 2

Production of 3-(1-adamantanecarbonyloxy)-1,1-bis(trifluoromethanesulfonyl)butane triphenylsulfonium salt

[Chemical Formula 78]

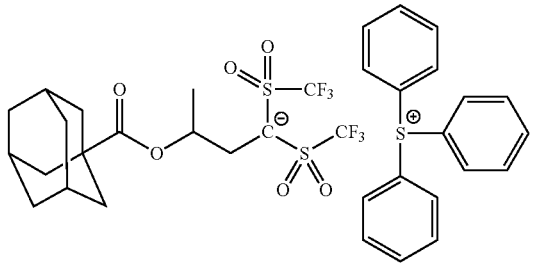

A glass flask was charged with 10 g (0.028 mol) of 3-hydroxy-1,1-bis(trifluoromethanesulfonyl)butane sodium salt, 16.7 g (0.084 mol) of 1-adamantanecarbonyl chloride, and 50 ml of acetonitrile, followed by stirring. Then, 8.6 g (0.084 mol) of triethylamine was added dropwise. After terminating the dropping, stirring was conducted at 55° C. for 4 hr. Then, the reaction liquid suspended was filtered to remove solid, and the solvent was distilled out of the filtrate by an evaporator. Then, 50 ml of chloroform was added to make a solution, and a 50 ml-water solution of 8.3 g (0.028 mol) of triphenylsulfonium chloride was added dropwise. After terminating the dropping, stirring was continued at room temperature for 1 hr. Then, the organic layer of the reaction liquid was washed three times with 40 ml of water, followed by distilling solvent off with an evaporator. The obtained liquid of a pale brown color was further washed three times with 40 ml of diethyl ether, followed by drying with a vacuum pump, thereby obtaining 9.1 g (yield 50%, purity 95%) of 3-(1-adamantanecarbonyl)oxy-1,1-bis(trifluoromethanesulfonyl) butane triphenylsulfonium salt as a pale brown color liquid.

Properties of 3-(1-adamantanecarbonyl)oxy-1,1-bis(trifluoromethanesulfonyl)butane triphenylsulfonium salt $^1$H NMR (measurement solvent: deuteriochloroform, standard substance: tetramethylsilane); δ=7.75 (m, 15H), 4.93 (m, 1H), 2.68 (brs, 1H), 2.44 (brs, 1H), 1.91 (s, 3H), 1.82 (s, 6H), 1.63 (brs, 6H), 1.18 (d, 3H)

$^{19}$F NMR (measurement solvent: deuteriochloroform, standard substance: tetramethylsilane); δ=−79.2 (brs, 6F)

Synthesis Example 3

Production of 3-phenylcarbonyloxy-1,1-bis(trifluoromethanesulfonyl)butane triphenylsulfonium salt

[Chemical Formula 79]

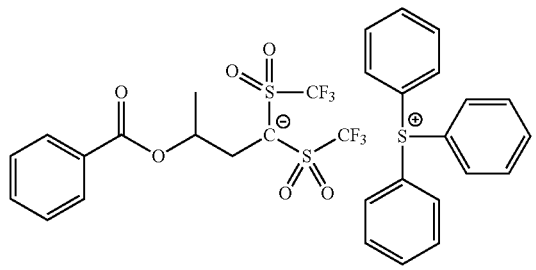

A glass flask was charged with 10 g (0.029 mol) of 3-hydroxy-1,1-bis(trifluoromethanesulfonyl)butane, 40 g of chloroform, 0.09 g (0.0009 mol) of methanesulfonic acid, followed by stirring. Then, 5.4 g (0.035 mol) of benzoic anhydride was added dropwise. After terminating the dropping, stirring was conducted at 55° C. for 4 hr. Then, the inside temperature was cooled until room temperature, and 15 g of water was added to the reaction liquid. Then, a 40 ml-water solution of 9.8 g (0.033 mol) of triphenylsulfonium chloride was added dropwise. After terminating the dropping, stirring was continued at room temperature for 1 hr. Then, the organic layer of the reaction liquid was washed five times with 40 ml of water, followed by distilling solvent off with an evaporator. The obtained liquid of a pale yellow color was further washed three times with 40 ml of diethyl ether, followed by drying with a vacuum pump, thereby obtaining 12.6 g (yield 62%, purity 95%) of 3-phenylcarbonyloxy-1,1-bis(trifluoromethanesulfonyl)butane triphenylsulfonium salt as a pale yellow color liquid.

Properties of 3-phenylcarbonyloxy-1,1-bis(trifluoromethanesulfonyl)butane triphenylsulfonium salt $^1$H NMR (measurement solvent: deuteriochloroform, standard substance: tetramethylsilane); δ=8.03 (m, 2H), 7.67 (m, 15H), 7.42 (m, 1H), 7.32 (m, 2H), 5.22 (m, 1H), 2.84 (brs, 1H), 2.62 (brs, 1H), 1.32 (d, 3H)

$^{19}$F NMR (measurement solvent: deuteriochloroform, standard substance: tetramethylsilane); δ=−79.1 (brs, 6F)

Evaluation of Photoacid Generator

Evaluation of 3-(1-adamantanecarbonyl)oxy 1,1-bis(trifluoromethanesulfonyl)butane triphenylsulfonium salt (PAG1), which had been produced as mentioned above, was conducted. For comparison, evaluation of existing (adamantan-1-ylmethyl)oxycarbonyl difluoromethanesulfonic acid triphenylsulfonium (PAG2) and nonafluorobutanesulfonic acid triphenylsulfonium salt (PAG3) was also conducted.

[Chemical Formula 80]

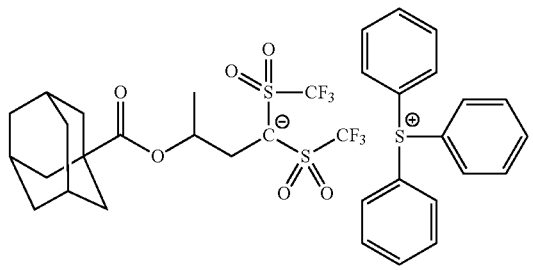

(PAG1)

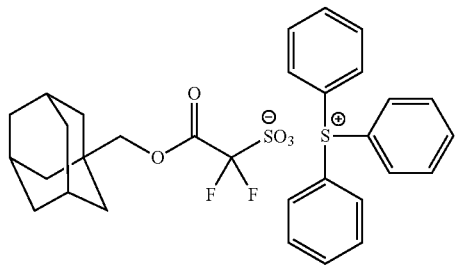

(PAG2)

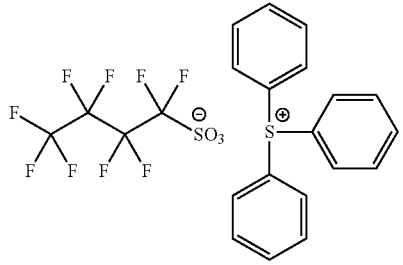

(PAG3)

1) Solubility in Resist Solvent

Using the above PAG1-3, solubility in propylene glycol monomethyl ether acetate (PGMEA), which is used as a resist solvent, was measured. The measurement results of solubility (parts by weight of PAG dissolved in 100 parts by weight of PGMEA) are shown in Table 1.

TABLE 1

| Example | PAG | Solubility |
| --- | --- | --- |
| Example 1 | PAG1 | not less than 0.1 |
| Comparative Example 1 | PAG2 | 0.3 |

As mentioned above, 3-(1-adamantanecarbonyl)oxy-1,1-bis(trifluoromethanesulfonyl)butane triphenylsulfonium salt (PAG1) of the present invention showed a solubility superior to that of the existing PAG (PAG2) having an adamantane skeleton.

2) Evaluations of Compatibility with Resist and Resolution of Resist

Resist materials were prepared by using PAG1 to PAG3 as acid generators and polymers (Resin 1-5) represented by the following formulas as the base resins. Furthermore, each composition was filtered by a membrane filter of 0.2 μm, thereby preparing each resist liquid.

[Chemical Formula 81]

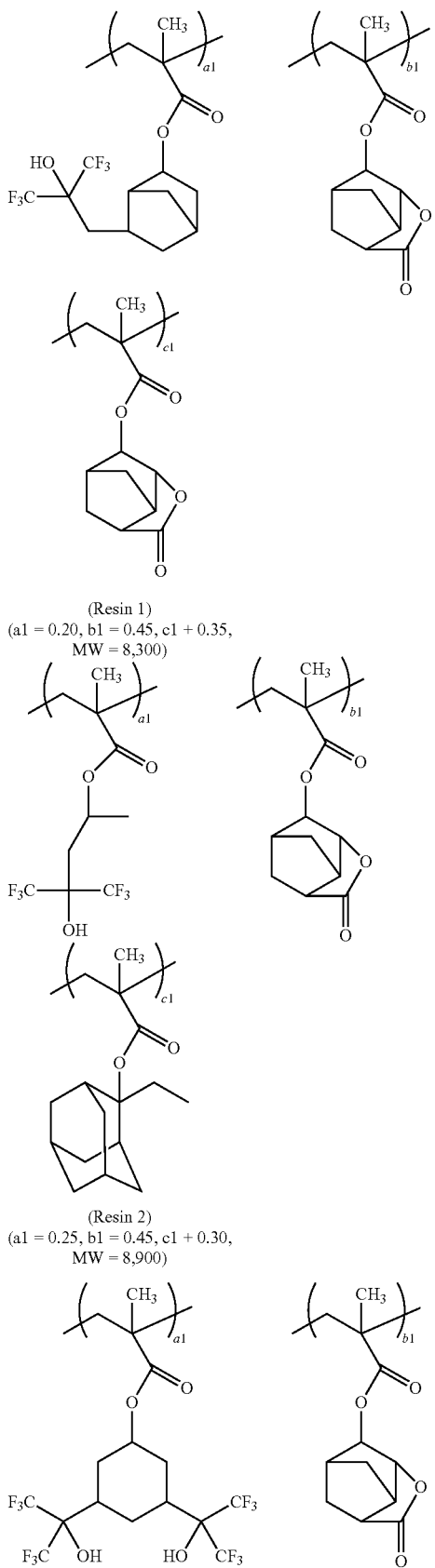

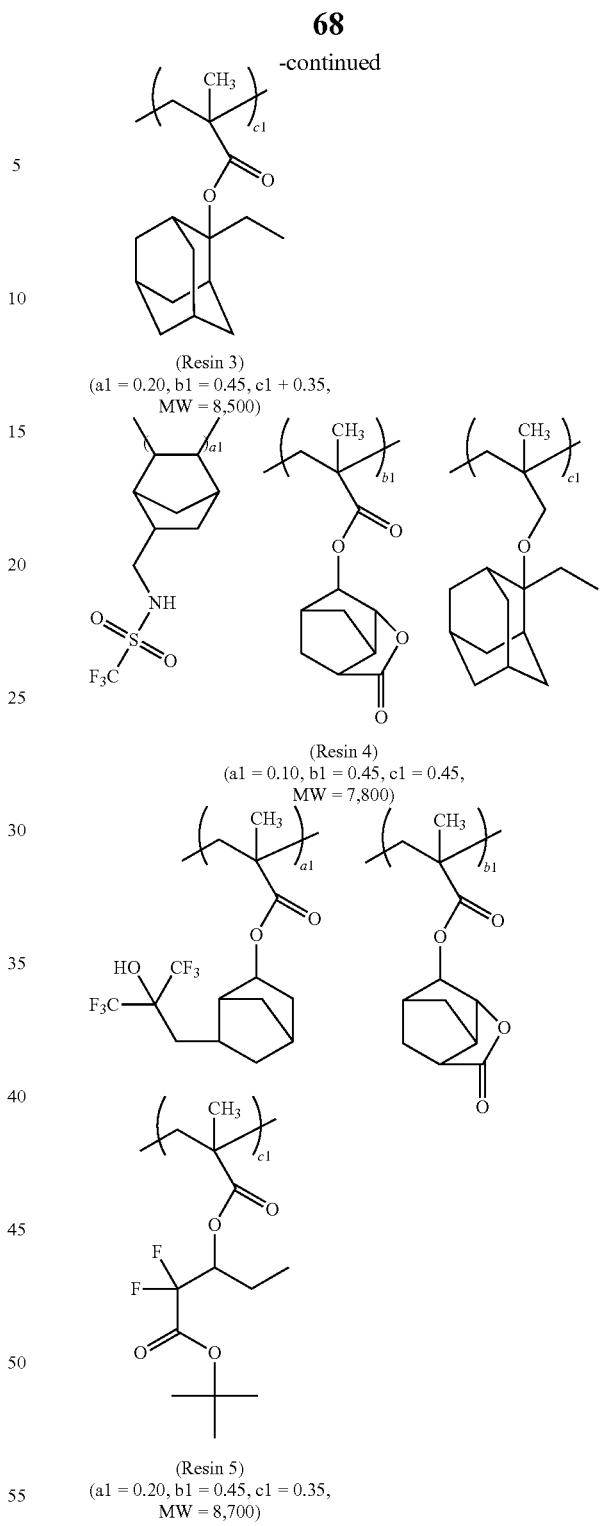

Then, all of the resist solutions were applied on silicon wafers by spin coating to obtain resist films having a film thickness of 250 nm. After conducting a prebaking at 110° C., exposure was conducted with 248 nm ultraviolet ray through a photomask, and then a post-exposure baking was conducted at 120° C. After that, development was conducted at 23° C. for 1 minute by using 2.38 wt % tetramethylammonium hydroxide aqueous solution. Composition and evaluation results of each resist are shown in Table 2.

TABLE 2

| Example | Resin (parts by wt.) | Acid Generator (parts by wt.) | Solvent (parts by wt.) | Compatibility | Pattern Shape |
|---|---|---|---|---|---|
| 2 | Resin 1 (40) | PAG 1 (1.0) | PGMEA (400) | Good | Clean rectangular |
| 3 | Resin 2 (40) | PAG 1 (1.0) | PGMEA (400) | Good | Clean rectangular |
| 4 | Resin 3 (40) | PAG 1 (1.0) | PGMEA (400) | Good | Clean rectangular |
| 5 | Resin 4 (40) | PAG 1 (1.0) | PGMEA (400) | Good | Clean rectangular |
| 6 | Resin 5 (40) | PAG 1 (1.0) | PGMEA (400) | Good | Clean rectangular |

For comparison, with respect to PAG2 and PAG3, evaluations of compatibility of PAG, when made into resists under the same condition as that of Example, and resolution of resists are shown in Table 3.

TABLE 3

| Comparative Example | Resin (parts by wt.) | Acid Generator (parts by wt.) | Solvent (parts by wt.) | Compatibility | Pattern Shape |
|---|---|---|---|---|---|
| 2 | Resin 1 (40) | PAG 2 (1.0) | PGMEA (400) | Good | Somewhat distorted rectangular |
| 3 | Resin 1 (40) | PAG 3 (1.0) | PGMEA (400) | Good | Somewhat head-swollen shape |
| 4 | Resin 2 (40) | PAG 2 (1.0) | PGMEA (400) | Good | Somewhat head-swollen shape |
| 5 | Resin 2 (40) | PAG 3 (1.0) | PGMEA (400) | Somewhat defective | Somewhat head-swollen shape |
| 6 | Resin 3 (40) | PAG 2 (1.0) | PGMEA (400) | Good | Somewhat head-swollen shape |
| 7 | Resin 3 (40) | PAG 3 (1.0) | PGMEA (400) | Somewhat defective | Somewhat head-swollen shape |
| 8 | Resin 4 (40) | PAG 2 (1.0) | PGMEA (400) | Good | Somewhat distorted rectangular |
| 9 | Resin 4 (40) | PAG 3 (1.0) | PGMEA (400) | Somewhat defective | Somewhat head-swollen shape |
| 10 | Resin 5 (40) | PAG 2 (1.0) | PGMEA (400) | Somewhat defective | Somewhat distorted rectangular |
| 11 | Resin 5 (40) | PAG 3 (1.0) | PGMEA (400) | Somewhat defective | Somewhat head-swollen shape |

From the results of Table 2 and Table 3, it was confirmed that 3-(1-adamantanecarbonyl)oxy 1,1-bis(trifluoromethanesulfonyl)butane triphenylsulfonium salt (PAG1) of the present invention showed a higher compatibility with resists as compared with conventional products and that resist materials using 3-(1-adamantanecarbonyl)oxy-1,1-bis(trifluoromethanesulfonyl)butane triphenylsulfonium salt (PAG1) of the present invention showed high resolutions.

The invention claimed is:

1. A compound that is an acid or a salt and has a fluorine-containing carbanion structure represented by the following general formula (1),

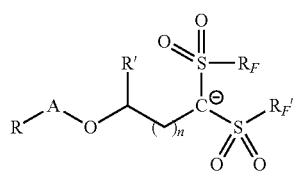

(1)

wherein
n represents an integer of 1-3;
R' represents a $C_{1-3}$ substituted or unsubstituted alkyl group;
R represents a $C_{1-10}$ straight-chain or branched alkyl group, a $C_{1-10}$ straight-chain or branched alkenyl group having a polymerizable double bond at an end portion at least, a $C_{3-20}$ alicyclic organic group, an organic group formed of a $C_{3-20}$ alicyclic organic group and a straight-chain alkylene group, a $C_{3-30}$ monocyclic or polycyclic lactone, or a $C_{6-20}$ aryl group;
in R, hydrogen atoms on the alkyl group, the alkenyl group, the alicyclic organic group, the organic group formed of the alicyclic organic group and the straight-chain alkylene group, the monocyclic or polycyclic lactone, and the aryl group may partially or entirely be replaced with fluorine, hydroxyl group, hydroxycarbonyl group, or $C_{1-6}$ straight-chain, branched or cyclic alkoxy group;
in R, two hydrogen atoms on the same carbon constituting the alkyl group, the alkenyl group, the alicyclic organic group, or the organic group formed of the alicyclic organic group and the straight-chain alkylene group may be replaced with a single oxygen atom to make a keto group;

in R, one of the hydrogen atoms on the alkyl group may be replaced with 2-acryloyloxy group or 2-methacryloyloxy group;

A represents any one of four groups represented by the following formula,

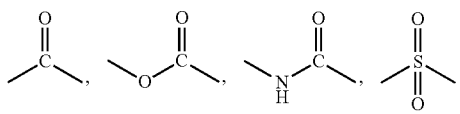

and each of $R_F$ and $R_F'$ independently represents a $C_{1-4}$ perfluoroalkyl group.

2. A compound according to claim 1 that is a salt having a fluorine-containing carbanion represented by the following general formula (3),

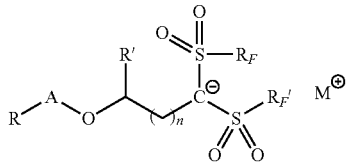

wherein n, R', R, A, $R_F$, and $R_F'$ have the same meanings as those of n, R', R, A, $R_F$, and $R_F'$ in the general formula (1) of claim 1; and $M^+$ represents a lithium ion, sodium ion, potassium ion, ammonium ion, or tetramethylammonium ion.

3. A salt formed of a fluorine-containing carbanion and an onium ion, said salt being represented by the following general formula (2),

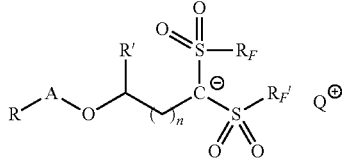

in the above general formula (2), n represents an integer of 1-3;

R' represents a hydrogen atom or a $C_{1-3}$ substituted or unsubstituted alkyl group;

R represents a $C_{1-10}$ straight-chain or branched alkyl group, a $C_{1-10}$ straight-chain or branched alkenyl group having a polymerizable double bond at an end portion at least, a $C_{3-20}$ alicyclic organic group, an organic group formed of a $C_{3-20}$ alicyclic organic group and a straight-chain alkylene group, a $C_{3-30}$ monocyclic or polycyclic lactone, or a $C_{6-20}$ aryl group;

in R, hydrogen atoms on the alkyl group, the alkenyl group, the alicyclic organic group, the organic group formed of the alicyclic organic group and the straight-chain alkylene group, the monocyclic or polycyclic lactone, and the aryl group may partially or entirely be replaced with fluorine, hydroxyl group, hydroxycarbonyl group, or $C_{1-6}$ straight-chain, branched or cyclic alkoxy group;

in R, two hydrogen atoms on the same carbon constituting the alkyl group, the alkenyl group, the alicyclic organic group, or the organic group formed of the alicyclic organic group and the straight-chain alkylene group may be replaced with a single oxygen atom to make a keto group;

in R, one of the hydrogen atoms on the alkyl group may be replaced with 2-acryloyloxy group or 2-methacryloyloxy group;

A represents any one of four groups represented by the following formula,

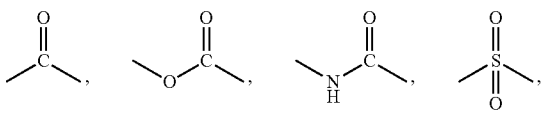

each of $R_F$ and $R_F'$ independently represents a $C_{1-4}$ perfluoroalkyl group; and $Q^+$ represents a sulfonium cation represented by the following general formula (a) or the following general formula (b), or an iodonium cation represented by the following general formula (c),

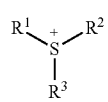

in the above general formula (a), $R^1$, $R^2$ and $R^3$ mutually independently represent substituted or unsubstituted $C_{1-10}$ straight-chain or branched alkyl groups, alkenyl groups or oxoalkyl groups; or substituted or unsubstituted $C_{6-18}$ aryl groups, aralkyl groups or aryloxoalkyl groups; or any two or more of $R^1$, $R^2$ and $R^3$ may be connected with each other to form a ring together with the sulfur atom in the formula (a),

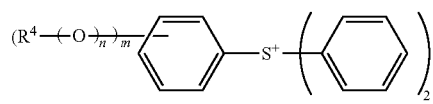

in the above general formula (b), $R^4$ represents a substituted or unsubstituted $C_{1-20}$ straight-chain, branched or cyclic alkyl group or alkenyl group; or substituted or unsubstituted $C_{6-14}$ aryl group; m represents an integer of 1-5, and n represents 0 (zero) or 1; as a substituent of $R^4$, it may contain a carbonyl group, hydroxyl group, ester, lactone, amino group, amide group, or ether linkage oxygen atom,

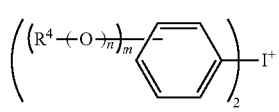

in the above general formula (c), $R^4$ represents a substituted or unsubstituted $C_{1-20}$ straight-chain, branched or cyclic alkyl group or alkenyl group; or substituted or unsubstituted $C_{6-14}$ aryl group; m represents an integer of 1-5, and n represents 0 (zero) or 1; as a substituent of $R^4$, it may contain a carbonyl group, hydroxyl group, ester, lactone, amino group, amide group, or ether linkage oxygen atom.

4. A photoacid generator for chemically amplified resist materials, comprising the salt according to claim 3 wherein said photoacid generator reacts with ultraviolet rays, far-ultraviolet rays, extreme ultraviolet rays (EUV), electron beam, X-ray, excimer laser, γ-ray, or a high energy ray of synchrotron radiation irradiation.

5. A resist material containing a base resin, a photoacid generator and a solvent, wherein the photoacid generator is the photoacid generator according to claim 4.

6. A photoacid generator for chemically amplified resist materials, which generates an acid having a fluorine-containing carbanion structure represented by the following general formula (4) by reacting with ultraviolet rays, far-ultraviolet rays, extreme ultraviolet rays (EUV), electron beam, X-ray, excimer laser, γ-ray, or a high energy ray of synchrotron radiation irradiation,

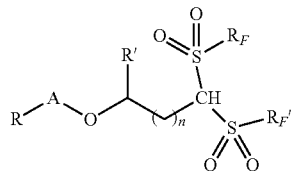

(4)

wherein
n represents an integer of 1-3;
R' represents a hydrogen atom or a $C_{1-3}$ substituted or unsubstituted alkyl group;
R represents a $C_{1-10}$ straight-chain or branched alkyl group, a $C_{1-10}$ straight-chain or branched alkenyl group having a polymerizable double bond at an end portion at least, a $C_{3-20}$ alicyclic organic group, an organic group formed of a $C_{3-20}$ alicyclic organic group and a straight-chain alkylene group, a $C_{3-30}$ monocyclic or polycyclic lactone, or a $C_{6-20}$ aryl group;
in R, hydrogen atoms on the alkyl group, the alkenyl group, the alicyclic organic group, the organic group formed of the alicyclic organic group and the straight-chain alkylene group, the monocyclic or polycyclic lactone, and the aryl group may partially or entirely be replaced with fluorine, hydroxyl group, hydroxycarbonyl group, or $C_{1-6}$ straight-chain, branched or cyclic alkoxy group;
in R, two hydrogen atoms on the same carbon constituting the alkyl group, the alkenyl group, the alicyclic organic group, or the organic group formed of the alicyclic organic group and the straight-chain alkylene group may be replaced with a single oxygen atom to make a keto group;
in R, one of the hydrogen atoms on the alkyl group may be replaced with 2-acryloyloxy group or 2-methacryloyloxy group;
A represents any one of four groups represented by the following formula,

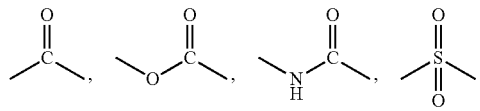

and each of $R_F$ and $R_F'$ independently represents a $C_{1-4}$ perfluoroalkyl group.

7. A resist material containing a base resin, a photoacid generator and a solvent, wherein the photoacid generator generates the acid having a fluorine-containing carbanion structure represented by the general formula (4) according to claim 6.

8. The resist material according to claim 7, wherein the base resin is a polymer prepared by polymerizing one monomer selected from the group consisting of olefins, fluorine-containing olefins, acrylates, methacrylates, fluorine-containing acrylates, fluorine-containing methacrylates, norbornene compounds, fluorine-containing norbornene compounds, styrene-series compounds, fluorine-containing styrene-series compounds, vinyl ethers and fluorine-containing vinyl ethers, or a copolymer prepared by copolymerizing at least two of the above monomers.

9. The resist material according to claim 7, wherein the base resin is a polymer compound containing a repeating unit represented by the following general formula (5),

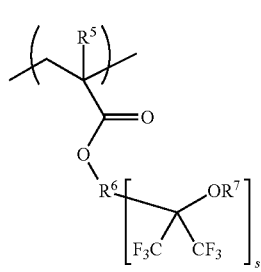

(5)

wherein
$R^5$ represents a hydrogen atom, halogen atom, hydrocarbon group, or fluorine-containing alkyl group;
$R^6$ is an alkyl group that is straight-chain or optionally branched, an alkyl group having a ring structure, an aromatic ring, or a complex substituent of them, and a part of that may be fluorinated;
$R^7$ is a hydrogen atom, a hydrocarbon group optionally branched, a fluorine-containing alkyl group, or a ring form having an aromatic or aliphatic ring, and may contain bond such as oxygen or carbonyl; and
s represents an integer of 1-2.

10. The resist material according to claim 9, wherein the repeating unit of the base resin is represented by the following general formula (6),

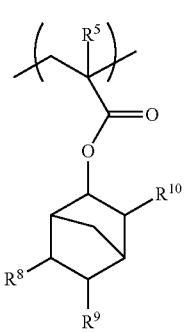

(6)

wherein
$R^5$ represents a hydrogen atom, halogen atom, hydrocarbon group, or fluorine-containing alkyl group; and any one of $R^8$, $R^9$ and $R^{10}$ is $CF_3C(CF_3)(OH)CH_2$— group, and the remaining two are hydrogen.

11. The resist material according to claim 9, wherein the repeating unit of the base resin is represented by the following general formula (7),

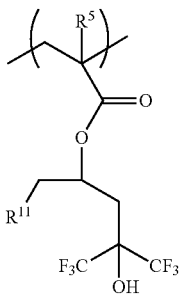

(7)

wherein
- $R^5$ represents a hydrogen atom, halogen atom, hydrocarbon group, or fluorine-containing alkyl group, and
- $R^{11}$ is a hydrogen atom, methyl group, ethyl group, n-propyl group, isopropyl group, n-butyl group, sec-butyl group, tert-butyl group, fluoromethyl group, difluoromethyl group, trifluoromethyl group, or perfluoroethyl group.

12. The resist material according to claim 9, wherein the repeating unit of the base resin is represented by the following general formula (8),

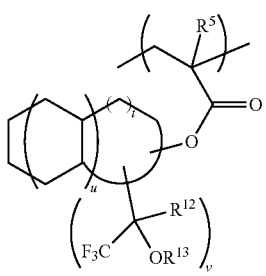

(8)

wherein
- $R^5$ represents a hydrogen atom, halogen atom, hydrocarbon group, or fluorine-containing alkyl group;
- $R^{12}$ represents a methyl group or trifluoromethyl group;
- $R^{13}$ is a hydrogen atom, a $C_{1-25}$ straight-chain, branched or cyclic hydrocarbon group or a group containing an aromatic hydrocarbon group, and a part of that may contain fluorine atom, oxygen atom or carbonyl bond;
- u represents an arbitrary integer of 0-2;
- t and v represent arbitrary integers of 1-8, and satisfy $v \leq t+2$; and
- in case that $R^{12}$-$R^{13}$ are in plural number, $R^{12}$-$R^{13}$ may respectively be the same or different.

13. The resist material according to claim 7, wherein the base resin contains a repeating unit represented by the following general formula (9),

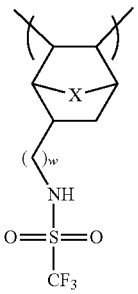

(9)

wherein
- X represents any of —$CH_2$—, —O—, and —S—; and
- w represents an integer of 2-6.

14. The resist material according to claim 7, wherein the base resin contains a repeating unit represented by the following general formula (23),

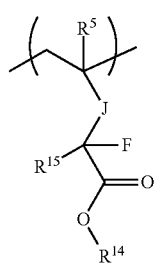

(23)

wherein
- $R^5$ represents a hydrogen atom, halogen atom, hydrocarbon group, or fluorine-containing alkyl group;
- $R^{15}$ represents a fluorine atom or fluorine-containing alkyl group,
- J represents a bivalent linking group; and
- $R^{14}$ is a hydrogen atom, a $C_{1-25}$ straight-chain, branched or cyclic hydrocarbon group or a group containing an aromatic hydrocarbon group, and a part of that may contain fluorine atom, oxygen atom or carbonyl bond.

15. The resist material according to claim 7, the resist material being a chemically amplified positive-type resist material, in which the base resin is insoluble or hardly soluble in a developing solution and becomes soluble in the developing solution by acid.

16. A pattern forming method, comprising:
   applying the resist material according to claim 7 on a substrate,
   exposing the resist material to a high energy ray having a wavelength of 300 nm or less through a photomask after a heating treatment, and
   developing the resist material using a developing solution, after a heat treatment according to need.

17. The pattern forming method according to claim 16, wherein the pattern forming method is an immersion lithography in which an ArF excimer laser of a wavelength of 193 nm is used, and in which water or a liquid, apart from water, having a refractive index higher than refractive index in the air is inserted between a substrate coated with the resist material and a projector lens.

18. A method for producing an acid having a fluorine-containing carbanion structure represented by the general formula (4)

(4)

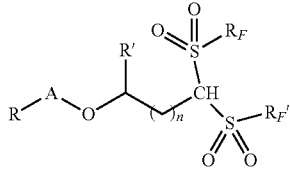

wherein
n represents an integer of 1-3;
R' represents a hydrogen atom or a $C_{1-3}$ substituted or unsubstituted alkyl group;
R represents a $C_{1-10}$ straight-chain or branched alkyl group, a $C_{1-10}$ straight-chain or branched alkenyl group having a polymerizable double bond at an end portion at least, a $C_{3-20}$ alicyclic organic group, an organic group formed of a $C_{3-20}$ alicyclic organic group and a straight-chain alkylene group, a $C_{3-30}$ monocyclic or polycyclic lactone, or a $C_{6-20}$ aryl group, wherein hydrogen atoms on the alkyl group, the alkenyl group, the alicyclic organic group, the organic group formed of the alicyclic organic group and the straight-chain alkylene group, the monocyclic or polycyclic lactone, and the aryl group may partially or entirely be replaced with fluorine, hydroxyl group, hydroxycarbonyl group, or $C_{1-6}$ straight-chain, branched or cyclic alkoxy group, and wherein two hydrogen atoms on the same carbon constituting the alkyl group, the alkenyl group, the alicyclic organic group, or the organic group formed of the alicyclic organic group and the straight-chain alkylene group may be replaced with a single oxygen atom to make a keto group, and wherein one of the hydrogen atoms on the alkyl group may be replaced with 2-acryloyloxy group or 2-methacryloyloxy group;
A represents any one of four groups represented by the following formulas

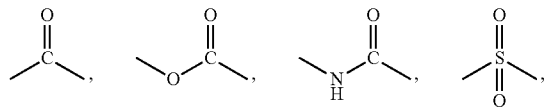

and each of $R_F$ and $R_F'$ independently represents a $C_{1-4}$ perfluoroalkyl group, comprising irradiating a photoacid generator according to claim 5 with ultraviolet rays, far-ultraviolet rays, extreme ultraviolet rays (EUV), electron beam, X-ray, excimer laser, γ-ray, or a high energy ray of synchrotron radiation irradiation.

19. 3-hydroxy-1,1-bis(trifluoromethanesulfonyl)butane represented by the following formula (11)

(11)

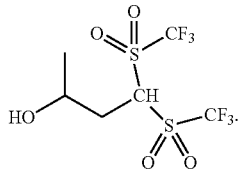

20. 3-methacryloyloxy-1,1-bis(trifluoromethanesulfonyl)-butane triphenylsulfonium salt represented by the following formula (12)

(12)

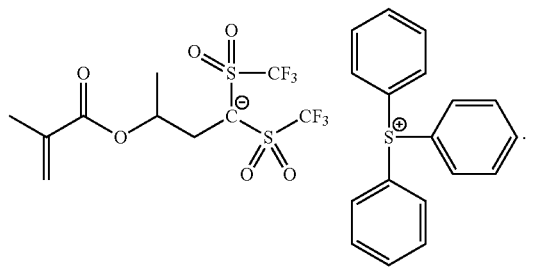

21. 3-(1-adamantanecarbonyloxy)-1,1-bis(trifluoromethane-sulfonyl)butane triphenylsulfonium salt represented by the following formula (13)

(13)

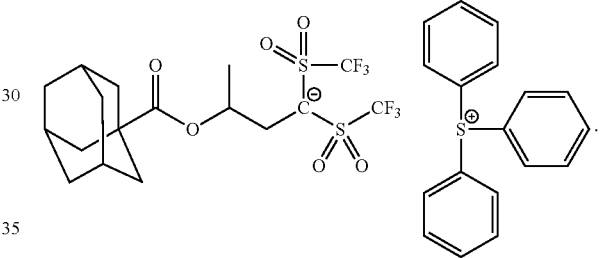

22. 3-phenylcarbonyloxy-1,1-bis(trifluoromethanesulfonyl)-butane triphenylsulfonium salt represented by the following formula (22)

(22)

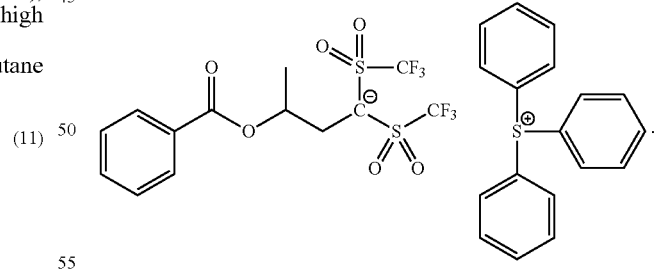

* * * * *